United States Patent
Shreve et al.

(10) Patent No.: US 9,765,896 B2
(45) Date of Patent: Sep. 19, 2017

(54) LOW VOLUME, PRESSURE ASSISTED, STEM AND SEAT VENT VALVE AND ASSOCIATED METHODS

(71) Applicant: Waters Technologies Corporation, Milford, MA (US)

(72) Inventors: Joshua A. Shreve, Franklin, MA (US); Steven D. Trudeau, Webster, MA (US)

(73) Assignee: Waters Technologies Corporation, Milford, MA (US)

( * ) Notice: Subject to any disclaimer, the term of this patent is extended or adjusted under 35 U.S.C. 154(b) by 92 days.

(21) Appl. No.: 14/381,976

(22) PCT Filed: Mar. 7, 2013

(86) PCT No.: PCT/US2013/029529
§ 371 (c)(1),
(2) Date: Aug. 28, 2014

(87) PCT Pub. No.: WO2013/134471
PCT Pub. Date: Sep. 12, 2013

(65) Prior Publication Data
US 2015/0014562 A1    Jan. 15, 2015

Related U.S. Application Data

(60) Provisional application No. 61/607,956, filed on Mar. 7, 2012.

(51) Int. Cl.
*F16K 1/38* (2006.01)
*F16K 1/42* (2006.01)
(Continued)

(52) U.S. Cl.
CPC .............. *F16K 1/42* (2013.01); *F16K 1/38* (2013.01); *F16K 31/0644* (2013.01);
(Continued)

(58) Field of Classification Search
CPC .............. F16K 1/38; F16K 1/42; F16K 25/00
(Continued)

(56) References Cited

U.S. PATENT DOCUMENTS 2,988,080 A * 6/1961 Rankl .................. F01L 3/06
                                              123/188.2
4,244,557 A * 1/1981 Polhede et al. ............... 251/167
(Continued)

OTHER PUBLICATIONS

Guiochon G, et al., Fundamental challenges and opportunities for preparative supercritical fluid chromatography. J Chromatogr A. Feb. 25, 2011;1218(8):1037-114.
(Continued)

*Primary Examiner* — Matthew W Jellett
(74) *Attorney, Agent, or Firm* — McCarter & English, LLP; Deborah M. Vernon; Vadim Cherkasov

(57) ABSTRACT

Exemplary embodiments are directed to vent valves, systems and methods generally involving a valve body that includes a seat retainer, a needle and a seat. The seat includes a bore extending there through and the needle includes a needle stem and a needle head. The seat is disposed inside the seat retainer. The needle stem is disposed inside the bore. The needle is configured to be pulled through the seat to stop flow through the bore. Exemplary embodiments are further directed to a system including a stem return spring mechanism and a solenoid return spring mechanism. A processing device is configured to actuate the solenoid return spring mechanism to permit the stem return spring mechanism to pull the needle through the seat to stop flow through the bore.

26 Claims, 21 Drawing Sheets

(51) Int. Cl.
  *F16K 31/06* (2006.01)
  *B01D 15/16* (2006.01)
  *B01D 15/40* (2006.01)
  *G01N 30/32* (2006.01)

(52) U.S. Cl.
  CPC ............ *B01D 15/163* (2013.01); *B01D 15/40* (2013.01); *G01N 2030/328* (2013.01)

(58) Field of Classification Search
  USPC ..... 251/129.15, 129.18, 322, 333, 339, 357, 251/359, 364, 365, 368
  See application file for complete search history.

(56) References Cited

U.S. PATENT DOCUMENTS

| | | | |
|---|---|---|---|
| 4,487,392 A | | 12/1984 | Eckenrode, Jr. |
| 4,905,960 A | * | 3/1990 | Barnhart et al. ......... 251/129.18 |
| 5,350,153 A | * | 9/1994 | Morinigo et al. ....... 251/129.16 |
| 5,556,075 A | * | 9/1996 | Weber ........................ 251/368 |
| 5,692,726 A | * | 12/1997 | Adachi et al. ............... 251/368 |
| 5,701,930 A | | 12/1997 | Russell |
| 6,073,648 A | | 6/2000 | Watson et al. |
| 6,295,975 B1 | * | 10/2001 | Yew et al. .................. 123/568.2 |
| 6,659,120 B2 | | 12/2003 | Kolb et al. |
| 7,681,650 B2 | * | 3/2010 | Telfer et al. .................. 166/386 |
| 2012/0126161 A1 | * | 5/2012 | Jeshani et al. ................ 251/337 |
| 2014/0191150 A1 | * | 7/2014 | Mikami et al. ............... 251/333 |
| 2015/0059864 A1 | * | 3/2015 | Shreve et al. ............. 137/15.17 |
| 2015/0059865 A1 | * | 3/2015 | Shreve et al. ............. 137/15.18 |

OTHER PUBLICATIONS

International Search Report for PCT/US2013/029529, date of mailing May 9, 2013.
Written Opinion of co-pending PCT International Application No. PCT/US2013/029529, dated May 9, 2013.

\* cited by examiner

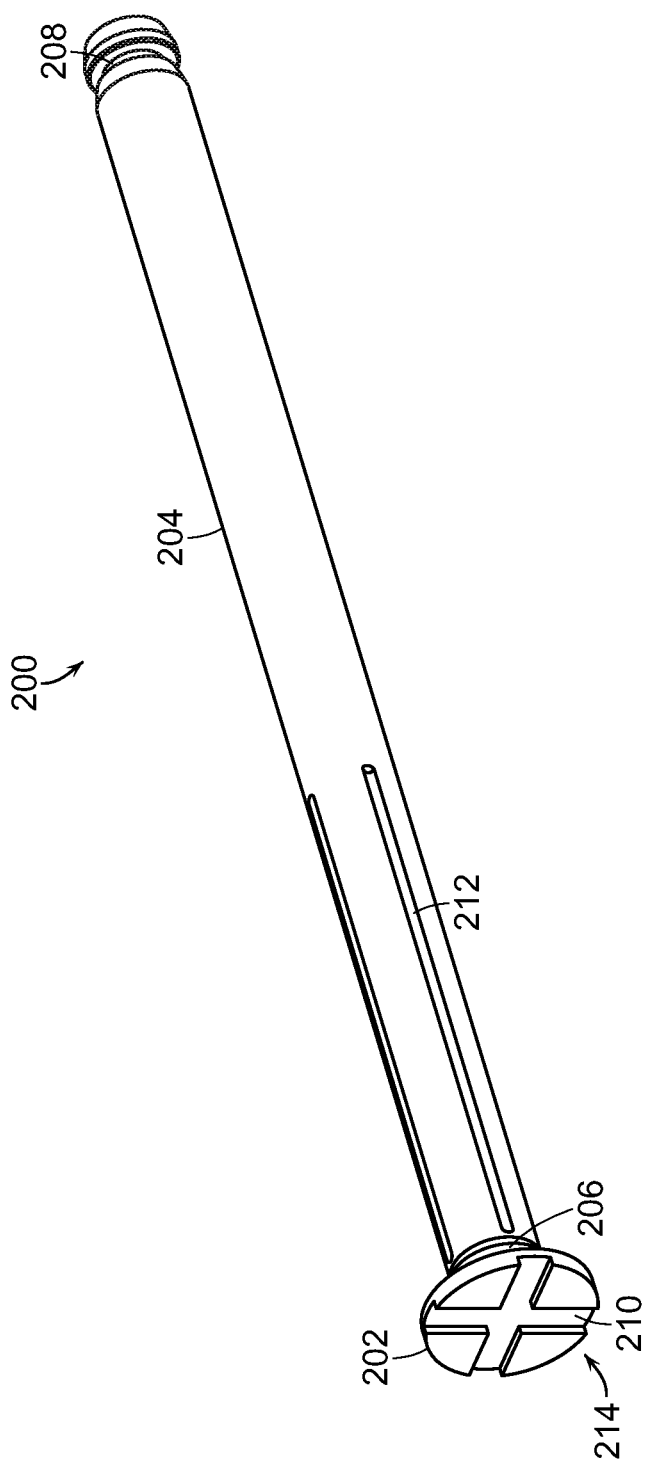

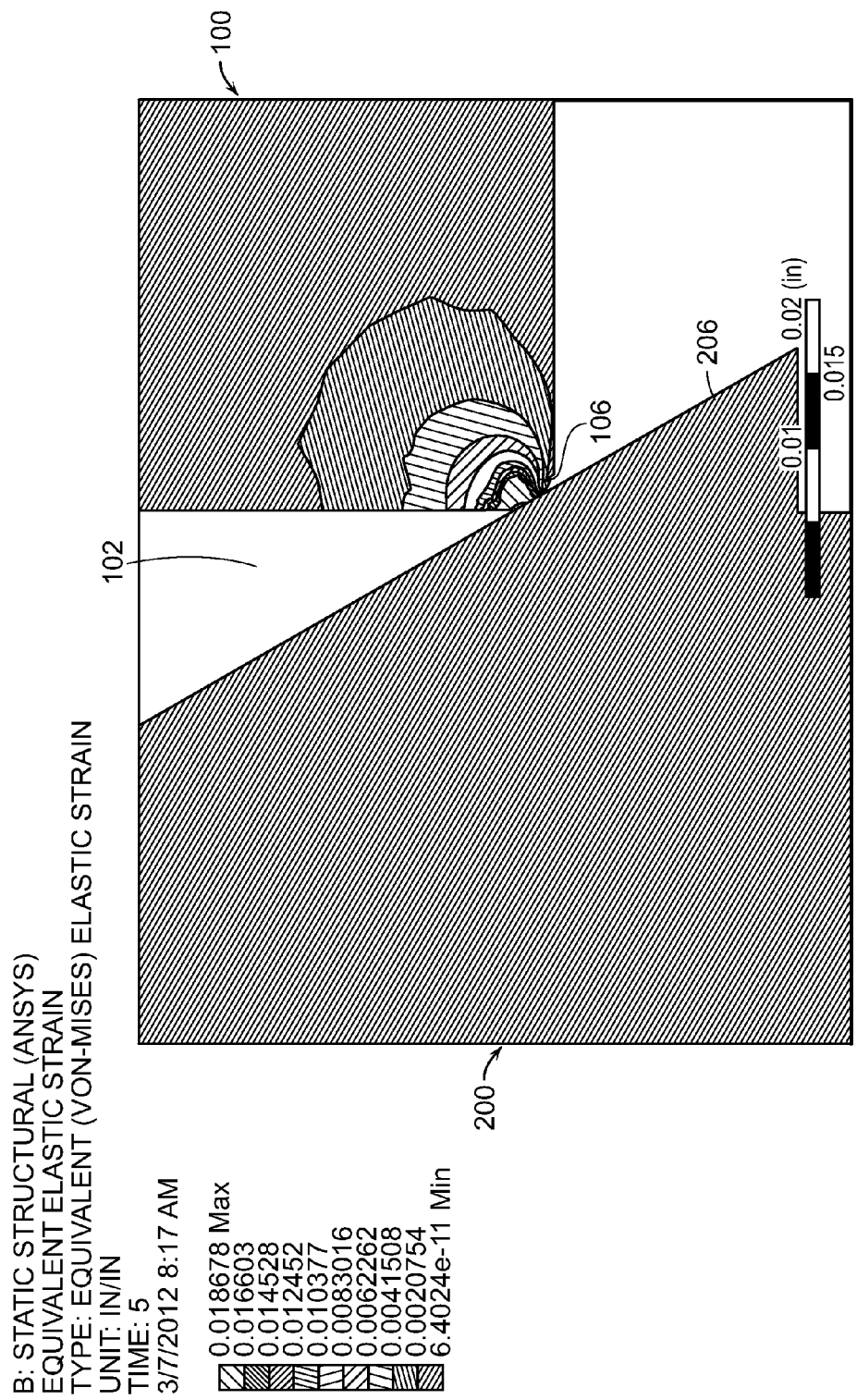

LOW VOLUME, PRESSURE ASSISTED, STEM AND SEAT VENT VALVE AND ASSOCIATED METHODS

RELATED APPLICATION

This application is a National Stage Application of International Application No. PCT/US2013/029529, filed Mar. 7, 2013, which claims priority to U.S. Provisional Application No. 61/607,956, filing date Mar. 7, 2012. Each of the foregoing applications is incorporated herein by reference in its entirety.

TECHNICAL FIELD

The present disclosure relates to vent valves and associated systems and methods and, in particular, to vent valves, systems and methods that minimize the exposed volume of the valve body to a fluid system and implement a system pressure to assist in sealing the vent valve.

BACKGROUND

Chromatographic techniques are important tools for the identification and separation of complex samples. The basic principle underlying chromatographic techniques is the separation of a mixture into individual components by transporting the mixture in a moving fluid through a retentive media. The moving fluid is typically referred to as the mobile phase and the retentive media is typically referred to as the stationary phase. The separation of the various constituents of the mixture is based on differential partitioning between the mobile and stationary phases. Differences in components' partition coefficient result in differential retention on the stationary phase, resulting in separation.

Conventionally, the methods of choice for chromatographic separations have been gas chromatography (GC) and liquid chromatography (LC). One major difference between GC and LC is that the mobile phase in GC is a gas, whereas the mobile phase in LC is a liquid. For example, in GC, a supply of inert carrier gas (mobile phase) is continually passed as a stream through a heated column containing porous sorptive media (stationary phase). A sample of the subject mixture is injected into the mobile phase stream and passed through the column, where separation of the mixture is primarily due to the differences in the volatile characteristics of each sample component at the temperature of the column. A detector, positioned at the outlet end of the column, detects each of the separated components as they exit the column. Although GC is typically a sensitive method of analysis, the high temperatures required in GC make this method unsuitable for high molecular weight biopolymers or proteins (heat will denature them), frequently encountered in biochemistry.

Conversely, LC is a separation technique in which the mobile phase is a liquid and does not require volatilization of the sample. Liquid chromatography that generally utilizes small packing particles and moderately high pressure is referred to as high-performance liquid chromatography (HPLC); whereas liquid chromatography that generally utilizes very small packing particles and high pressure is referred to as ultra-high performance liquid chromatography (UHPLC). In HPLC and UHPLC the sample is forced by a liquid at high pressure (the mobile phase) through a column that is packed with a stationary phase composed of irregularly or spherically shaped particles, a porous monolithic layer, or a porous membrane.

Because LC uses liquid as the mobile phase, LC techniques are capable of analyzing higher molecular weight compounds and, in some cases, LC can be used to prepare large scale batches of purified protein(s). However, in contrast, GC techniques are typically more sensitive and readily allow for the separation of single chiral materials. Thus, GC has conventionally been used to isolate and determine the relative purity of a chiral compound, e.g., by determining the enantiomeric excess (% ee) or the diastereomeric excess (% de) of a particular sample. As with most chromatographic techniques, the limiting factor in both GC and LC has been the ability to obtain and/or reproduce pure sample separations, each of which are typically dependent on the apparatus, methods, and conditions employed, e.g., flow rate, column size, column packing material, solvent gradient, etc.

Supercritical Fluid Chromatography is another chromatographic technique, which has typically been used in preparative applications. For every liquid substance there is a temperature above which it can no longer exist as a liquid, no matter how much pressure is applied. Likewise, there is a pressure above which the substance can no longer exist as a gas no matter how much the temperature is raised. These points are called the supercritical temperature and supercritical pressure, and define the boundaries on a phase diagram for a pure substance (FIG. 1). At this point, the liquid and vapor have the same density and the fluid cannot be liquefied by increasing the pressure. Above this point, where no phase change occurs, the substance acts as a supercritical fluid (SF). Thus, SF can be described as a fluid obtained by heating above the critical temperature and compressing above the critical pressure. There is a continuous transition from liquid to SF by increasing temperature at constant pressure or from gas to SF by increasing pressure at constant temperature.

The term SFC, while typically standing for Supercritical Fluid Chromatography, does not require or mean that supercritical conditions are obtained during or maintained throughout the separation. That is, columns do not have to be always operated in the critical region of the mobile phase. For example, in the event that the mobile phase includes a modifier (e.g., $CO_2$ and methanol as a modifier), the mobile phase is often in its subcritical region (e.g., a highly compressed gas or a compressible liquid rather than a supercritical fluid). In fact, as Guiochon et al note in section 2.3 of their review article entitled "Fundamental challenges and opportunities for preparative supercritical fluid chromatography" Journal of Chromatography A, 1218 (2011) 1037-1114: "It is obvious that SFC has very often been and still is run under subcritical conditions." Thus, the term SFC is not limited to processes requiring supercritical conditions.

Because SFC typically uses $CO_2$, SFC processes are inexpensive, innocuous, eco-friendly, and non-toxic. There is typically no need for the use of volatile solvent(s) (e.g., hexane). Finally, the mobile phase in SFC processes (e.g., $CO_2$ together with any modifier/additive as a SF, highly compressed gas, or compressible liquid) typically have higher diffusion constants and lower viscosities relative to liquid solvents. The low viscosity means that pressure drops across the column for a given flow rate is greatly reduced. The increased diffusivity means longer column length can be used.

SUMMARY

Exemplary embodiments of the present technology include vent valves, systems and methods that minimize the exposed volume of the valve body and/or implement a system pressure to assist in sealing the vent valve, especially in $CO_2$-based chromatography systems.

In accordance with embodiments of the present technology, exemplary vent valves and associated systems and methods are disclosed that involve a valve body that includes a seat retainer, a needle and a seat. The seat includes a bore extending therethrough. The needle includes a needle stem and a needle head. In particular, the seat is disposed inside the seat retainer. The needle stem is disposed inside the bore. The needle can be configured to be pulled through the seat to stop flow through the bore. Conversely, the needle can be configured to be pushed through the seat to start flow through the bore.

Embodiments of the exemplary vent valves and associated systems and methods can include one or more of the following features. In certain embodiments, the needle includes an exterior coating of, e.g., a gold, platinum, ceramic, polymer, or the like. The needle head diameter can be greater than a needle stem diameter. Further, the needle includes an angular sealing surface between the needle stem and the needle head for self-centering and aligning the needle during translation through the seat. During sealing, the angular sealing surface can be pulled against a bore edge of the seat to stop flow through the bore. During at least the first sealing between the angular sealing surface and the bore edge, a plastic deformation of the bore edge can occur when the angular sealing surface is pulled against the bore edge. The plastic deformation conforms the bore edge geometry to a complimentary angular sealing surface geometry to ensure a durable and/or tight seal against the angular sealing surface.

In embodiments, the seat is fabricated from, e.g., 30% carbon fiber filled PEEK, a filled or unfilled grade PEEK, a filled or unfilled grade of polyimide plastic, or the like. The polyimide plastic can be, e.g., Vespel® commercially available from E. I. du Pont de Nemours & Company, Wilmington, Del., USA. In some exemplary embodiments, the seat includes or defines a unitary structure. In other exemplary embodiments, the seat includes a plurality of components. In certain embodiments a bore diameter of the seat is greater than the needle stem diameter to permit the needle stem to pass through the bore. The needle head is further include at least one head groove on a needle head face. It should be understood that in other embodiments, more than one head groove can be used, e.g., two, three, four, and the like. The needle stem can also include at least one stem groove. Similarly, it should be understood that in other embodiments, more than one stem groove can be used, e.g., two, three, four, five, six, and the like. Pulling the needle through the seat to stop flow through the bore reduces an exposed volume of the valve body. In addition, a pressure force, i.e., a pressure assist from the system pressure, can be implemented to enhance the durable and/or tight seal of the needle against the angular sealing surface.

In accordance with another embodiment of the present disclosure, exemplary methods of closing a vent valve are disclosed, generally involving providing a valve body that includes a seat retainer, a needle and a seat. The seat includes a bore extending therethrough. The needle includes a needle stem and a needle head. In particular, the seat is disposed inside the seat retainer. The needle stem is disposed inside the bore. The exemplary method includes pulling the needle through the seat to stop flow through the bore.

Embodiments of the above exemplary methods can include one or more of the following features. In certain embodiments, the needle head diameter is greater than a needle stem diameter. The needle can include an angular sealing surface, e.g., tapered, slanted, or the like, between the needle stem and the needle head for self-centering and aligning the needle during translation through the seat. The angular sealing surface can be pulled against a bore edge of the seat to stop flow through the bore. Embodiments of the exemplary method can include plastically deforming the bore edge geometry to ensure a tight seal against the angular sealing surface. In addition, a pressure force, i.e., a pressure assist from the system pressure, can be provided to enhance the durable and/or tight seal against the angular sealing surface.

In accordance with another embodiment of the present disclosure, exemplary systems for closing a vent valve are disclosed, generally involving a valve body that includes a seat retainer, a needle, a seat, a stem return spring mechanism and a solenoid return spring mechanism. The seat includes a bore extending therethrough. The needle includes a needle stem and a needle head. In particular, the seat is disposed inside the seat retainer. The needle stem can is disposed inside the bore. The stem return spring mechanism connects to a distal needle stem end opposing the needle head. Further, the solenoid return spring mechanism can be in communication with the stem return spring mechanism. The exemplary system further includes a processing device configured to actuate the solenoid return spring mechanism to permit the stem return spring mechanism to pull the needle through the seat to stop flow through the bore.

The vent valves, systems, and methods of the present disclosure provide numerous advantages. For example, one or more embodiments of the present technology provide increased improved pressure control in chromatographic applications, such as $CO_2$-based chromatography applications. In a $CO_2$-based chromatography system it is desirable to have the ability to vent the system when it is not in use. If the vent significantly adds to the system volume the ability of the back pressure regulator to control pressure can be compromised. Embodiments of the valves, systems, and methods in accordance with the present disclosure utilize a specific needle and seat design to minimize internal volume of the valve in a closed position resulting in increased pressure control.

BRIEF DESCRIPTION OF THE DRAWINGS

The foregoing and other features and advantages provided by the present disclosure will be more fully understood from the following description of exemplary embodiments when read together with the accompanying drawings, in which:

FIG. 9A-C illustrate an exemplary embodiment of a needle with stem grooves and exemplary seat plastic deformation according to the present disclosure;

DESCRIPTION OF EXEMPLARY EMBODIMENTS

Figure 1:
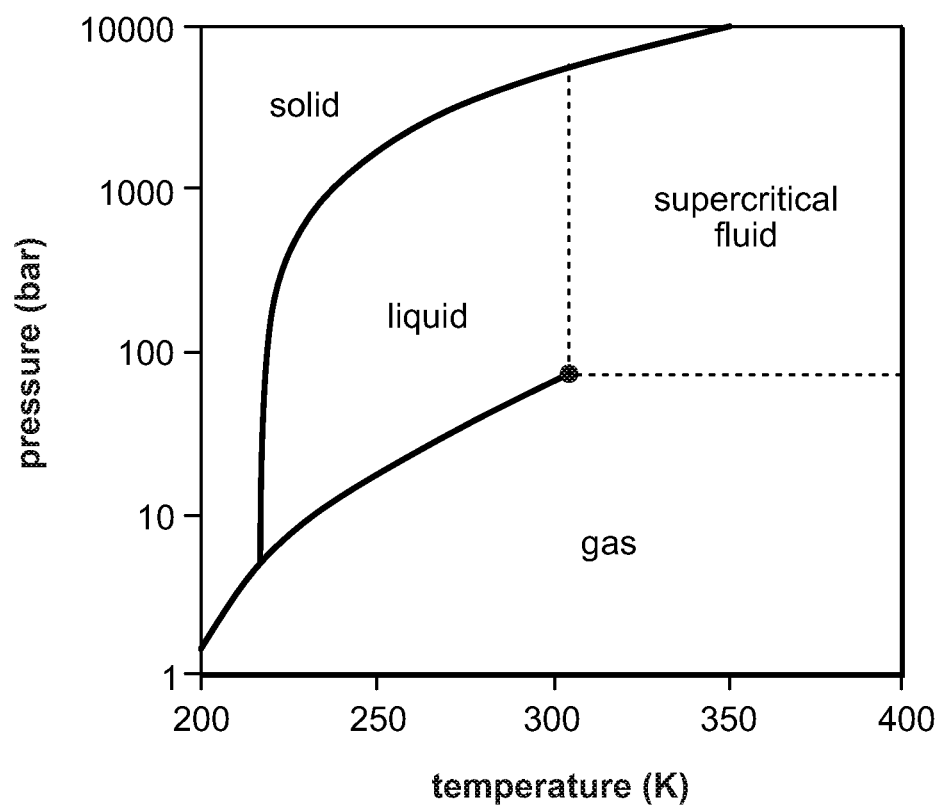
FIG. 1 is an exemplary graph of the physical state of a substance in relation to a temperature and pressure associated with the substance.

SFC can be adapted as a hybrid between HPLC and GC apparatuses, where the predominant modification is replacement of either the liquid or gas mobile phase with a supercritical fluid (or near supercritical fluid) mobile phase, such as with $CO_2$. In SFC, the mobile phase is initially pumped as a liquid or gas and is brought into the supercritical region by heating or pressurizing the mobile phase above its supercritical temperature/pressure prior to entry into a column. As the mobile phase passes through an injection valve, the sample is introduced into the supercritical stream, and the mixture is then transferred into a column. The mixture passes through the column (at supercritical or liquid state) and into the detector.

In general, the mobile phase in SFC processes have the ability to act both as substance carriers (like the mobile phases in GC), and dissolve substances readily (like the solvents used in LC). In addition to generally having lower viscosities and better diffusion profiles similar to those of certain gases, the mobile phase in SFC processes also generally have high densities and dissolving capacities similar to those of certain liquids. For example, SFs' high densities (0.2-0.5 gm/cm$^3$) provide for their remarkable ability to dissolve large, non-volatile molecules, e.g., supercritical or near supercritical $CO_2$ readily dissolves n-alkanes, di-n-alkyl phthalates, and polycyclic and aromatic compounds. Since the diffusion of solutes in a SFC mobile phase is about ten times greater than that in liquids (about three times less than in gases), this results in a decrease in resistance to mass transfer in the column and allows for fast high resolution separation. Also, the solvation strength of the mobile phase in SFC processes is directly related to the fluid density. Thus, the solubility of solids can be easily manipulated by making slight changes in temperatures and pressures.

Another important property of the mobile phase in SFC processes is that it provides high resolution chromatography at much lower temperatures. For example, an analyte dissolved in supercritical $CO_2$ can be recovered by reducing the pressure and allowing the sample to evaporate under ambient laboratory conditions. This property is useful when dealing with thermally unstable analytes, such as high molecular weight biopolymers or proteins.

The combination of one or more mechanical or column changes to an SFC instrument (e.g., a $CO_2$-based chromatography instrument) coupled with the inherent properties of the SFC itself, allows for the separation of both chiral and achiral compounds, and has become increasingly predominant in the field of preparatory separations for drug discovery and development. Despite considerable advances in SFC technology, there is a need to develop innovative methods and apparatuses that improve the use of SFC. Controlling and stabilizing the pressure in an SFC instrument by one or more process and/or improving one or more of the instrumental characteristics of the system, may lead to, amongst others, improved compound separation and efficiency.

For example, better resolution and increased flow rate would decrease cycle times (i.e., shorter cycle times) and allow for improved separation of both chiral and achiral compounds, and lead to an overall increase in laboratory efficiency; increased speed and throughput would decrease the amount of solvent and cost(s) associated with SFC; and the ability to further integrate SFC with other detection methods, such as Mass Spectrometry (MS), Flame Ionization Detectors (FID), and Ultraviolet/Visible (UV) detectors, would improve the mainstream use of SFC using a mobile phase including $CO_2$ as an eco-friendly, yet effective, alternative method for the fast, complete, and sensitive analysis of analytes.

It is generally desirable to have the ability to vent an SFC system using a $CO_2$-based mobile phase when it is not in use. However, if the vent valve significantly adds to the system volume, the ability of the back pressure regulator to control pressure in the SFC system can be compromised. Conventional vent valves are generally configured to push the needle into the seat to stop flow through the vent valve. In this configuration, a pressure assist can be implemented to open the vent valve. However, the seal of the needle against the seat and/or the bore inside the seat add to the exposed close volume of the vent valve. An increased pressure assist ensures the valve seals properly at higher pressures where non-pressure assisted valves tend to leak. The exposed volume of the vent valve requires conventional systems to compress a larger volume to increase pressure. In particular, the maximum rate of pressurization is directly related to the solvent stiffness times the flow rate divided by the system volume. Increased volume thereby decreases the response of these conventional system and leads to more lag and/or slower control attributes.

Exemplary embodiments of the present technology include vent valves, systems and methods that minimize the exposed volume of the valve body and/or implement a system pressure to assist in sealing the vent valve, especially in $CO_2$-based chromatography systems.

In accordance with embodiments of the present disclosure, exemplary vent valves and associated systems and methods are disclosed that involve a valve body that includes a seat retainer, a needle and a seat. The seat includes a bore extending therethrough. The needle includes a needle stem and a needle head. In particular, the seat is disposed inside the seat retainer. The needle stem is disposed (at least partially) inside the bore. The needle can be configured to be pulled through the seat to stop flow through the bore. Conversely, the needle can be configured to be pushed through the seat to start flow through the bore. The exemplary vent valves and associated systems and methods can further include a processing device configured to actuate a solenoid return spring mechanism to permit the stem return spring mechanism to pull the needle through the seat to stop flow through the bore.

As used herein, the terms "downstream" and "upstream" refer to relative locations in a system flow, wherein upstream refers to being associated with an earlier portion of the system flow compared to a later portion of the system flow and downstream refers to being associated with a later portion of the system flow compared to an earlier portion of the system flow.

Figure 2:
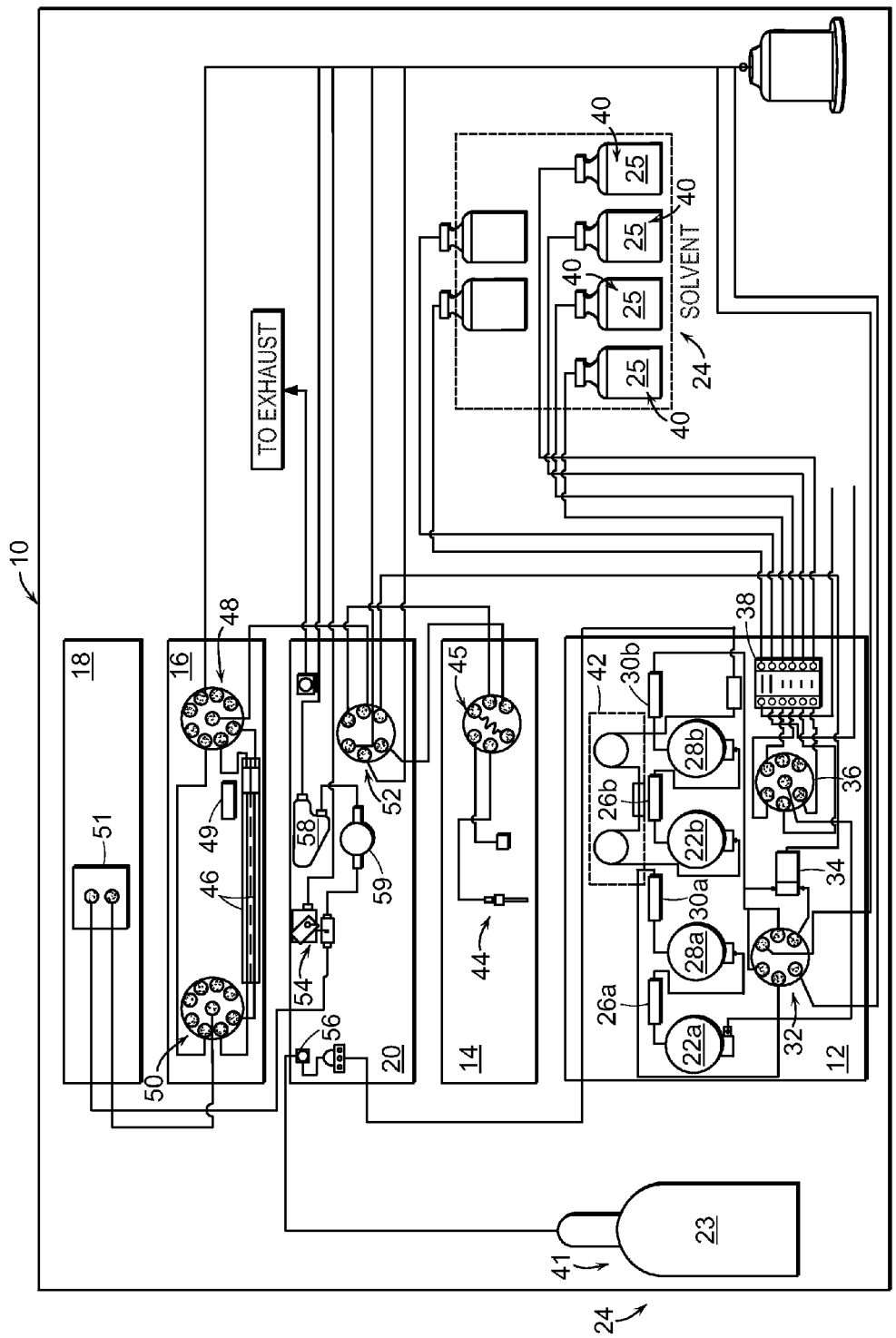
FIG. 2 is a block diagram of an exemplary pressurized flow system.

FIG. 2 is a block diagram of an exemplary pressurized flow system, which in the present embodiment is implemented as a $CO_2$-based chromatography system 10 (hereinafter "system 10"). While the present embodiment is illustrative of a $CO_2$-based chromatography system 10 operated at or near supercritical conditions, those skilled in the art will recognize that exemplary embodiments of the present disclosure can be implemented as other pressurized flow systems and that one or more system components of the present disclosure can be implemented as components of other pressurized systems. System 10 can be configured to detect sample components of a sample using chromatographic separation in which the sample is introduced into a mobile phase that is passed through a stationary phase. System 10 can include one or more system components for managing and/or facilitating control of the physical state of the mobile phase, control of the pressure of the system 10, introduction of the sample to the mobile phase, separation of the sample into components, and/or detection of the sample components, as well as venting of the sample and/or mobile phase from the system 10.

Figure 3:
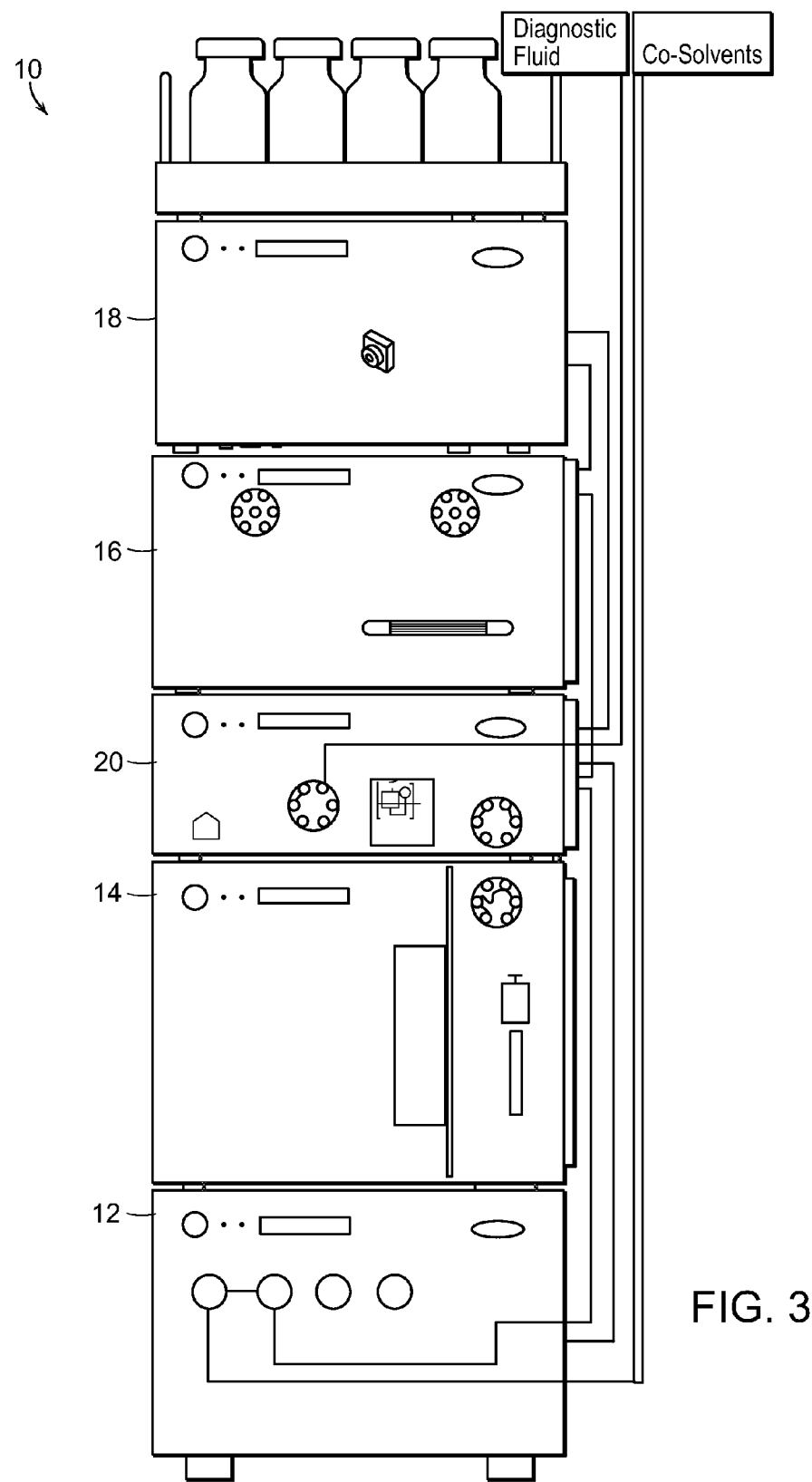
FIG. 3 is a block diagram of an exemplary arrangement of an embodiment of the system of FIG. 2.
Figure 4:
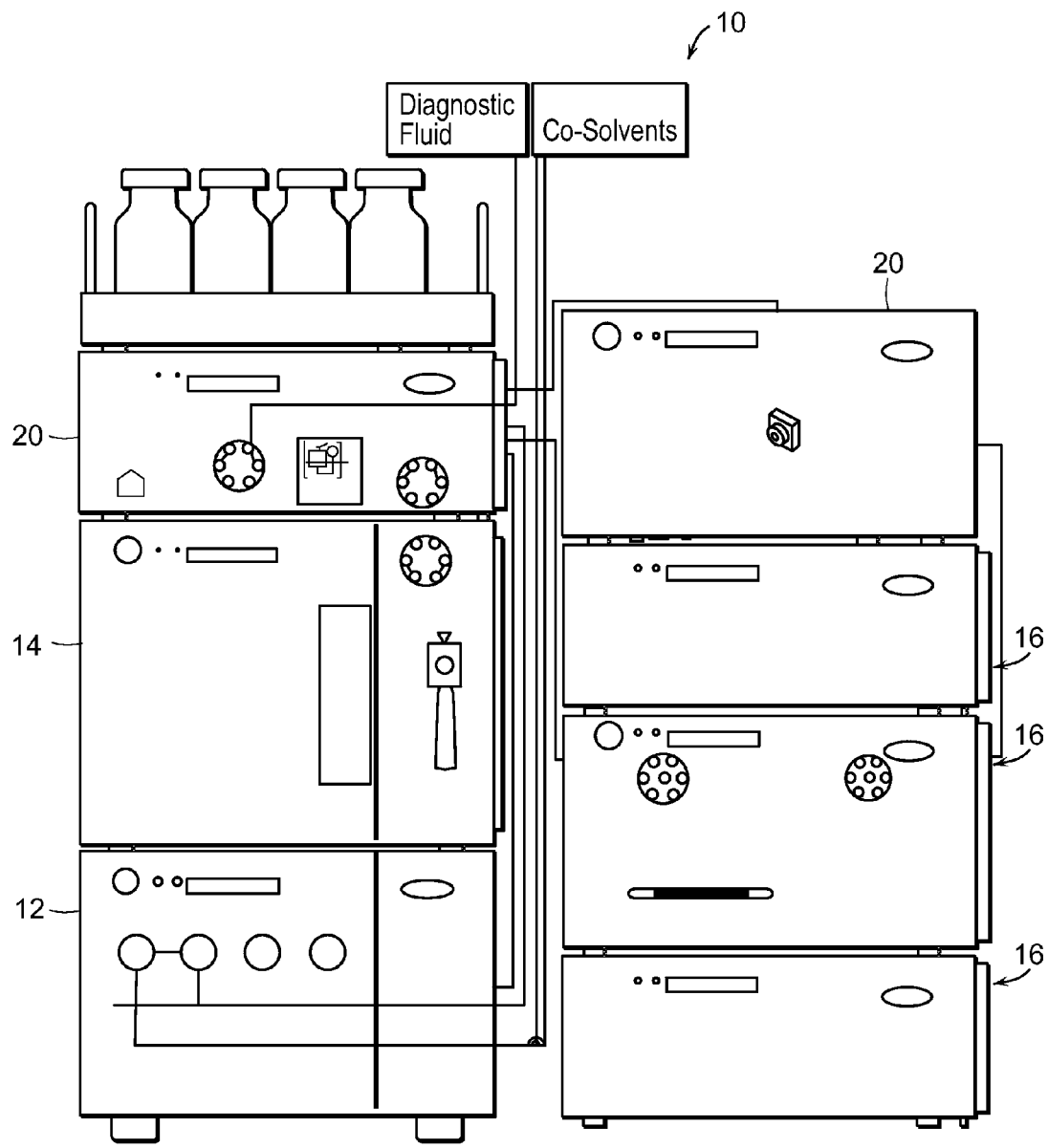
FIG. 4 is a block diagram of another exemplary arrangement of an embodiment of the system of FIG. 2.

In the present embodiment, the system 10 can include a solvent delivery system 12, a sample delivery system 14, a sample separation system 16, a detection system 18 (e.g., a PDA detector), and a system/convergence manager 20. In some embodiments, the system components can be arranged in one or more stacks. As another example, in one embodiment, the system components of the system 10 can be arranged in a single vertical stack (FIG. 3). The system components of the system 10 can be arranged in multiple stacks (FIG. 4). Those skilled in the art will recognize that other arrangements of the components of the system 10 are possible. Furthermore, while embodiments of the system 10 have been illustrated as including system components 12, 14, 16, 18, and 20, those skilled in the art will recognize that embodiments of the system 10 can be implemented as a single integral unit, that one or more components can be combined, and/or that other configurations are possible.

The solvent delivery system 12 can include one or more pumps 22a and 22b configured to pump one or more solvents 24, such as mobile phase media 23 (e.g., carbon dioxide) and/or modifier media 25 (i.e., a co-solvent, such as, e.g., methanol, ethanol, 2-methoxyethanol, isopropyl alcohol, or dioxane), through the system 10 at a predetermined flow rate. For example, the pump 22a can be in pumping communication with the modifier media 25 to pump the modifier media 25 through the system 10, and the pump 22b can be in pumping communication with the mobile phase media 23 to pump the mobile phase media 23 through the system 10. An output of the pump 22a can be monitored by a transducer 26a and an output of the pump 22b can be monitored by a transducer 26b. The transducers 26a and 26b can be configured to sense the pressure and/or flow rate associated with the output of the solvent 24 from the pumps 22a and 22b, respectively. Each pump 22a and/or 22b further includes a pump control valve configured to be actuated into, e.g., a flow position, a block position, a vent position, and the like.

The outputs of the pumps 22a and 22b can be operatively coupled to an input of accumulators 28a and 28b, respectively. The accumulators 28a and 28b are refilled by the outputs of the pumps 22a and 22b, respectively, and can contain an algorithm to reduce undesired fluctuations in the flow rate and/or pressure downstream of the pumps 22a and 22b, which can cause detection noise and/or analysis errors on the system 10. An output of the accumulator 28a can be monitored by a transducer 30a and an output of the accumulator 28b can be monitored by a transducer 30b. The transducers 30a and 30b can be configured to sense pressure and/or flow rate at an output of the accumulators 28a and 28b, respectively. The outputs of the accumulators 28a and 28b can be operatively coupled to a multiport valve 32, which can be controlled to vent the solvent 24 (e.g., mobile phase media 23 and modifier media 25) being pumped by the pumps 22a and 22b and/or to output the solvent 24 to a mixer 34. The mixer 34 can mix the modifier media 25 and the mobile phase media 23 output from the pumps 22a and 22b, respectively (e.g., after first passing through the accumulators 28a and 28b) and can output a mixture of the mobile phase media 23 and the modifier media 25 to form a solvent stream (i.e., mobile phase) that flows through the system 10. The output of the mixer 34 can be operatively coupled to the system/convergence manager 20 as discussed in more detail below.

In exemplary embodiments, the solvent delivery system 12 can include a multiport solvent selection valve 36 and/or a degasser 38. The solvent selection valve 36 and/or the degasser 38 can be operatively disposed between an input of the pump 22a and solvent containers 40 such that the solvent selection valve 36 and/or the degasser 38 are positioned upstream of the pump 22a. The solvent selection valve 36 can be controlled to select the modifier media 23 to be used by the system 10 from one or more solvent containers 40 and the degasser 38 can be configured to remove dissolved gases from the media modifier 23 before the media modifier 23 is pumped through the system 10.

In exemplary embodiments, the solvent delivery system 12 can include a pre-chiller 42 disposed between an input of the pump 22b and a solvent container 41 such that the pre-chiller is disposed upstream of the input to the pump 22b and downstream of the solvent container 41. The pre-chiller 42 can reduced the temperature of the mobile phase media 23 before it is pumped through the system 10 via the pump 22b. In the present embodiment, the mobile phase media 23 can be carbon dioxide. The pre-chiller can decrease the temperature of the carbon dioxide so that the carbon dioxide is maintained in a liquid state (i.e., not a gaseous state) as it is pumped through at least a portion of the system 10. Maintaining the carbon dioxide in a liquid state can facilitate effective metering of the carbon dioxide through the system 10 at the specified flow rate.

The pumps 22a and 22b can pump the solvent 24 through the system 10 to pressurize the system 10 to a specified pressure, which may be controlled, at least in part, by the system/convergence manager 20. In exemplary embodiments, the system 10 can be pressurized to a pressure between about 700 psi and about 18,000 psi or about 1,400 psi and about 8,000 psi. In one embodiment, the system 10 can be pressurized to a pressure of about 6,000 psi. By pressurizing the system 10 at these pressure levels (such as those pressure levels described above), the solvent stream (i.e., mobile phase) can be maintained in a liquid state before transitioning to a supercritical fluid state or near supercritical state (e.g., highly-compressed gas or compressible liquid) for a chromatographic separation in a column, which can be accomplished by raising the temperature of the pressurized solvent stream.

The sample delivery system 14 can select one or more samples to be passed through the system 10 for chromatographic separation and detection. The sample delivery system 14 can include a sample selection and injection member 44 and a multi-port valve 45. The sample selection and injection member 44 can include a needle through which the sample can be injected into the system 10. The multiport valve 45 can be configured to operatively couple the sample selection and injection member 44 to an input port of the system/convergence manager 20.

The sample separation system 16 can receive the sample to be separated and detected from the sample delivery system 14, as well as the pressurized solvent stream from the solvent delivery system 12, and can separate components of the sample passing through the system 10 to facilitate detection of the samples using the detection system 18. The sample separation system 16 can include one or more columns 46 disposed between an inlet valve 48 and an outlet valve 50. The one or more columns 46 can have a generally cylindrical shape that forms a cavity, although one skilled in the art will recognize that other shapes and configurations of the one or more columns is possible. The cavity of the columns 46 can have a volume that can at least partially be filled with retentive media, such as hydrolyzed silica, such as $C_8$ or $C_{18}$, or any hydrocarbon, to form the stationary phase of the system 10 and to promote separation of the components of the sample. The inlet valve 48 can be disposed upstream of the one or more columns can be configured to select which of the one or more columns 46, if any, receives the sample. The outlet valve 50 can be disposed downstream of the one or more columns 46 to selectively receive an output from the one or more columns 46 and to pass the output of the selected one or more columns 46 to the detection system 18. The columns 46 can be removably disposed between the valves 48 and 50 to facilitate replacement of the one or more columns 46 to new columns after use. In some embodiments, multiple sample separation systems 16 can be included in the system 10 to provide an expanded quantity of columns 46 available for use by the system 10 (FIG. 4).

In exemplary embodiments, the sample separation system 16 can include a heater 49 to heat the pressurized solvent stream 24 prior and/or while the pressured solvent stream 24 passes through the one or more columns 46. The heater 49 can heat the pressurized solvent stream to a temperature at which the pressured solvent transitions from a liquid state to a supercritical fluid state so that the pressurized solvent stream passes through the one or more columns 46 as a supercritical fluid.

Referring again to FIG. 2, the detection system 18 can be configured to receive components separated from a sample by the one or more columns 46 and to detect a composition of the components for subsequent analysis. In an exemplary embodiment the detection system 18 can include one or more detectors 51 configured to sense one of more characteristics of the sample components. For example, in one embodiment, the detectors 51 can be implemented as one or more photodiode arrays.

The system/convergence manager 20 can be configured to introduce a sample from the sample delivery system 14 into the pressurized solvent stream flowing from the solvent delivery system 12 and to pass the solvent stream and sample to the sample separation system 16. In the present embodiment, the system/convergence manager 20 can include a multiport auxiliary valve 52 which receives the sample injected by the sample delivery system 14 through a first inlet port and the pressurized solvent stream from the solvent delivery system 12 through a second inlet port. The auxiliary valve 52 can mix the sample and the solvent stream and output the sample and solvent stream via an outlet port of the multiport auxiliary valve 52 to an inlet port of the inlet valve 48 of the sample separation system 16.

The system/convergence manager 20 can also be configured to control the pressure of the system 10 and to facilitate cooling, heating and/or venting of the solvent from the system 10, and can include a vent valve 54, a shut off valve 56, a back pressure regulator 58, and a transducer 59. The vent valve 54 can be disposed downstream of the detection system 18 can be configured to decompress the system 10 by venting the solvent from the system 10 after the solvent has passed through the system 10. The shut-off valve 56 can be configured to disconnect the solvent supply from the inlet of the pump 22b of the solvent delivery system to prevent the solvent from being pumped through the system 10. An exemplary vent valve 54 will be described in more detail below. In exemplary embodiments, the shut-off valve 56 can be incorporated into one or more pumps 22a and 22b or anywhere else in the system 10 if a controller is attached.

The back pressure regulator 58 can control the back pressure of the system 10 to control the flow of the mobile phase and sample through the column, to maintain the mobile phase in the supercritical fluid state (or, in some embodiments, in a near supercritical state, such as, a highly-compressed gas or compressible liquid) as the mobile phase passes through the one or more columns 46 of the sample separation system 16, and/or to prevent the back pressure from forcing the mobile phase reversing its direction a flow through the one or more columns 46. Embodiments of the back pressure regulator 58 can be configured to regulate the pressure of the system 10 so that the physical state of the solvent stream (i.e., mobile phase) does not change uncontrollably upstream of and/or within the back pressure regulator 58. The transducer 59 can be a pressure sensor disposed upstream of the back pressure regulator 58 to sense a pressure of the system 10. The transducer 59 can output a feedback signal to a processing device which can process the signal to control an output of an actuator control signal from the processing device.

Figure 5:
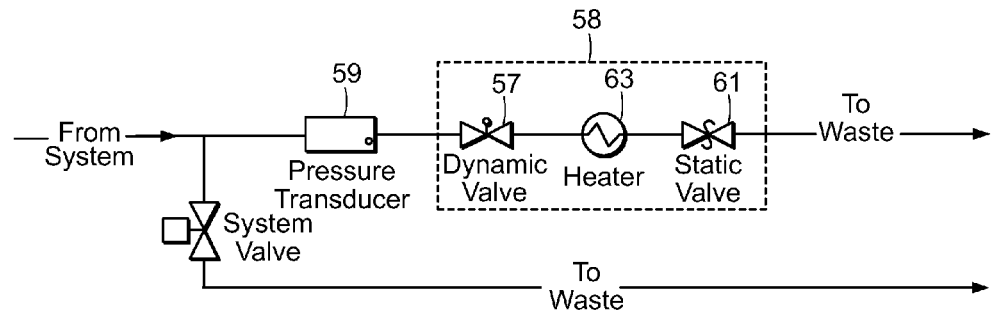
FIG. 5 is a flow diagram of a mobile phase through a system manager portion of the an exemplary embodiment of the pressurized flow system.

In exemplary embodiments, as shown in FIG. 5, the back pressure regulator 58 can include a dynamic pressure regulator 57, a static pressure regulator 61, and a heater 63. The static pressure regulator 61 can be configured to maintain a predetermined pressure upstream of the back pressure regulator 58. The dynamic pressure regulator 57 can be disposed upstream of the static pressure regulator 61 and can be configured to set the system pressure above the predetermined pressure maintained by the static regulator 61. The heater 63 can be disposed downstream of the dynamic pressure regulator 57 and can be disposed in close proximity to the static pressure regulator 61 to heat the solvent stream as it passes through the static pressure regulator 61 to aid in control of the physical state of the solvent as it passes through the static pressure regulator 61.

In summary, an exemplary operation of the system 10 can pump mobile phase media 23 and modifier media 25 at a specified flow rate through the system 10 as a solvent stream (i.e., mobile phase) and can pressurize the system 10 to a specified pressure so that the solvent stream maintains a liquid state before entering the sample separation system 16. A sample can be injected into the pressurized solvent stream by the sample delivery system 14, and the sample being carried by the pressurized solvent stream can pass through the sample separation system 16, which can heat the pressurized solvent stream to transition the pressurized solvent stream from a liquid state to a supercritical fluid state. The sample and the supercritical fluid solvent stream can pass through at least one of the one or more columns 46 in the sample separation system 16 and the column(s) 46 can separate components of the sample from each other. The separated components can pass the separated components to the detection system 18, which can detect one or more characteristics of the sample for subsequent analysis. After the separated sample and solvent pass through the detection system 18, the solvent and the sample can be vented from the system 10 by the system/convergence manager 20.

In other embodiments, the system 10 described herein can also be used for preparatory methods and separations. Typical parameters, such as those described above, may be manipulated to achieve effective preparatory separations. For example, the system 10 described herein confers the benefit of exerting higher flow rates, larger columns, and column packing size, each of which contributes to achieving preparatory separation and function, while maintaining little or no variability in overall peak shape, peak size, and/or retention time(s) when compared to respective analytical methods and separations thereof. Thus, in one embodiment, the present disclosure provides $CO_2$-based chromatography systems 10 which are amendable to preparatory methods and separations with high efficiency and correlation to analytical runs.

Figure 6:
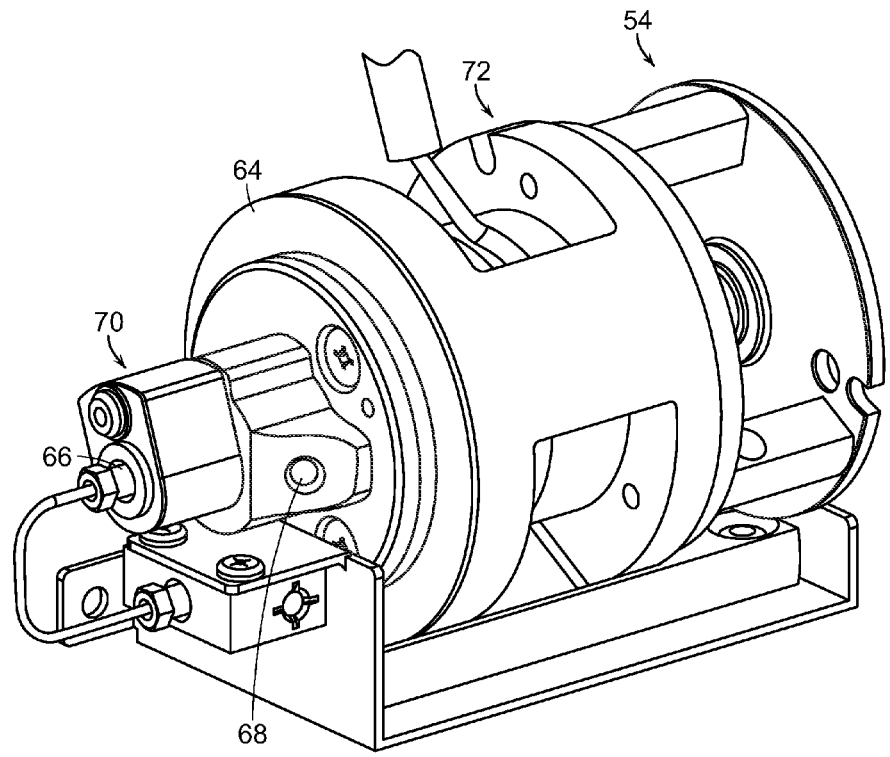
FIG. 6 is an exemplary embodiment of a vent valve according to the present disclosure.

With reference to FIG. 6, an exemplary vent valve 54 is depicted, including a valve body 64, a pressurized inlet port 66 and an outlet port 68. The vent valve 54 can have two sections, i.e., a vent valve actuator section 72 and a vent valve head section 70. As will be discussed in greater detail below, the vent valve head section 70 includes the seat retainer, needle and seat to be implemented in the exemplary vent valve 54. It should be understood that the dimensions and/or configurations of the vent valve 54 are merely exemplary and other embodiments can have different dimensions and/or configurations.

Figure 7A:
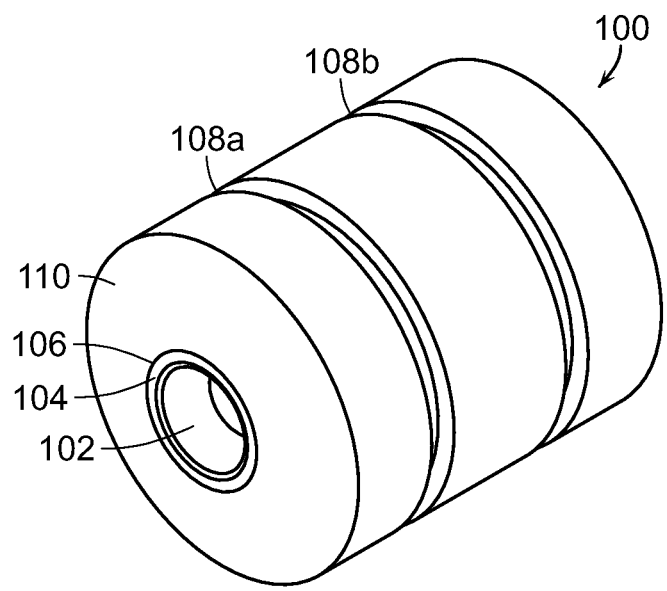
FIGS. 7A and 7B are exemplary embodiments of a seat according to the present disclosure.
Figure 7B:
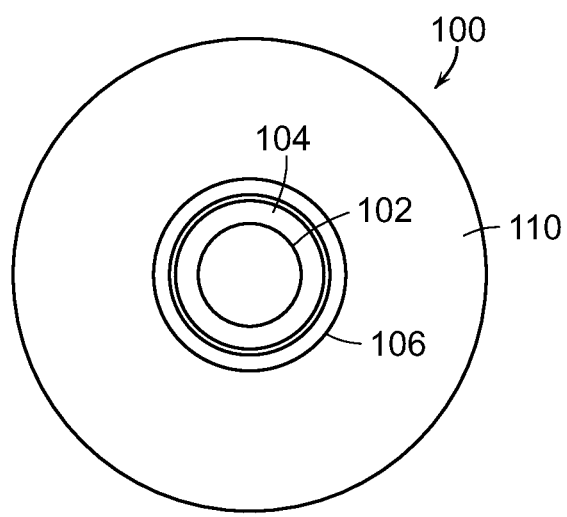

Turning to FIGS. 7A and 7B, an exemplary seat 100 is illustrated, including a bore 102 extending therethrough. The bore 102 is greater in diameter than a needle stem diameter to ensure the needle stem can pass through unimpeded. It should therefore be understood that the bore 102 dimension can differ based on the needle stem being implemented. The bore 102 can include a chamfered outlet 104, e.g., angled, beveled, outwardly sloping, and the like, to create a larger opening surface area than the bore 102 diameter for sealing against the needle head. For example, the chamfered outlet 104 can be at about, e.g., 15°, 20°, 25°, 30°, 35°, 40°, 45°, and the like. In other embodiments, the chamfered outlet 104 can be at an angle less than the taper of the angled sealing surface of the needle. For example, the chamfered outlet 104 angle can be half or less of the angle of the taper of the angled sealing surface of the needle. The larger opening surface area created by the chamfered outlet 104 can assist in centering and/or guiding the needle head as it is pulled into the bore 102. The edge adjoining the chamfered outlet 104 of the bore 102 and outer side surfaces 110 of the seat 100 can be defined by the bore edge 106.

The seat 100 may include circumferential seat grooves 108a and 108b for identification of particular seat 100 geometries. For example, different geometries of the exemplary seat 100 may include varying patterns of seat grooves 108a and 108b to aid in identification of the particular seat 100. Thus, although illustrated with two seat grooves 108a and 108b, other embodiments of the exemplary seat 100 can have less and/or more seat grooves, e.g., zero, one, two, three, four, five, and the like, depending on the seat 100 geometry. As would be understood by those of ordinary skill in the art, seat 100 can be inserted into a seat retainer and may be manufactured from a material which prevents undesired motion of the seat 100 within the seat retainer. In some exemplary embodiments, the seat retainer can include protrusions, e.g., spikes, ridges, and the like, configured and dimensioned to securely retain the seat 100 within the seat retainer. Although illustrated as a seat 100 having a unitary structure, it should be understood that in some exemplary embodiments, the seat 100 can include a plurality of components.

Figure 8A:
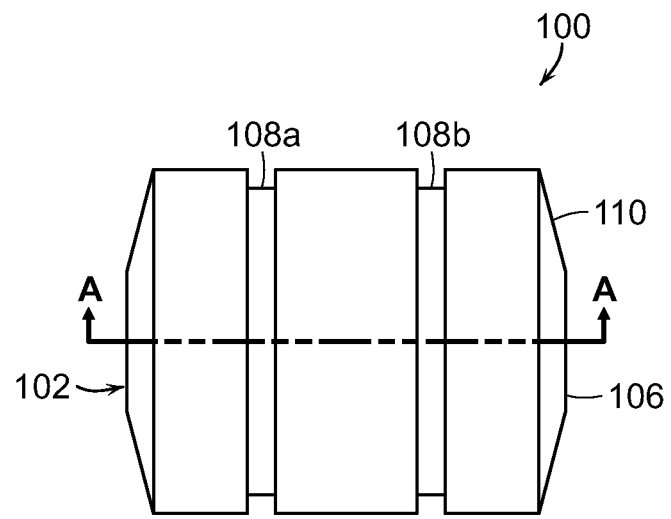
FIGS. 8A and 8B are side and cross-sectional views of exemplary embodiments of a seat according to the present disclosure.
Figure 8B:
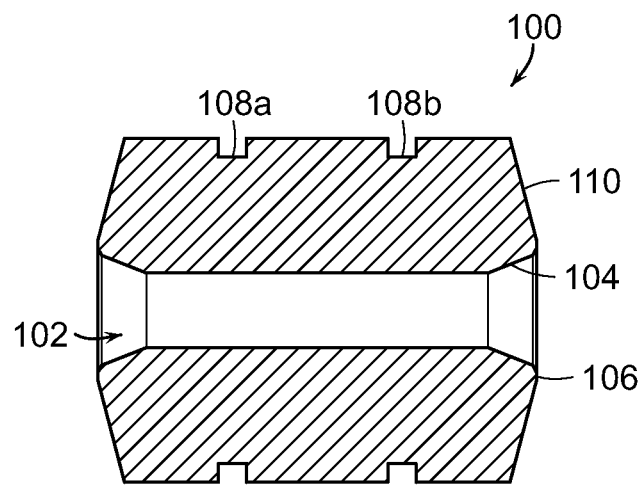

FIGS. 8A and 8B depict a side view and a cross-sectional side view, respectively, of the exemplary seat 100. In particular, FIG. 8B depicts a cross-sectional view of the seat 100 along plane "A". As can be seen, the bore 102 passes through the length of the seat 100 and the chamfered outlets 104 on both sides of the bore 102 increase the opening surface area at the outer side surfaces 110 to a surface area greater than the bore 102 diameter. The outer side surfaces 110 can be, e.g., angled, parallel to the seat grooves 108a and 108b, or the like. For example, in FIG. 8B, the outer side surfaces 110 define angled sides.

Turning now to FIG. 9A, an exemplary needle 200 is illustrated, including a needle head 202 and a needle stem 204. The diameter of the needle head 202 is greater than the diameter of the needle stem 204 to provide a durable and/or tight seal between the needle head 202 and the seat 100 when the needle stem 204 is pulled through the bore 102. The diameter of the needle stem 204 can be configured and dimensioned to pass unimpeded through the bore 102. In particular, the diameter of the needle stem 204 can be slightly smaller than the diameter of the bore 102 to permit the needle stem 204 to pass through the bore 102, while supporting the needle 200. Thus, no matter which dimensions and/or configurations of the needle 200 and/or seat 100 are being implemented, the diameter of the needle stem 204 will always be slightly smaller than the diameter of the bore 102.

The needle can include an angular sealing surface 206 between the needle stem 204 and the needle head 202. In particular, the angular sealing surface 206 can act as a transition and/or connection area between the needle stem 204 and the needle head 202. The angular sealing surface 206 can be, e.g., sloping, convex, concave, or the like. Thus, when the needle stem 204 is pulled and/or translated through the bore 102 of the seat 100 to stop flow through the bore 102, the seat 100 can act as, e.g., a bushing, and the angular sealing surface 106 can self-center, e.g., align, guide, or the like, the needle 100 to ensure the needle head 202 is centered with respect to the bore 102. The needle 200 can further include an exterior coating of, e.g., gold, platinum, ceramic, polymer, and the like. The exterior coating can protect the needle 200 from, e.g., corrosion, pitting, and the like, caused by the system pressure loads and/or solvents involved during operation. The exterior coating can further protect the needle 200 from metal-to-metal contact with, e.g., the inlet port 66 when the vent valve 54 is actuated into an open position. For example, the needle head 202 can come in direct contact against a portion of the inlet port 66 (e.g., metal, in which the inlet port 66 is formed from) when the needle stem 204 has been translated through the bore 102 to create a flow path between the angular sealing surface 206 and the bore edge 106. Alternatively, rather than the entire needle 200 including the exterior coating, only the needle head 202 and/or the angular sealing surface 206 can include the exterior coating.

Figure 9C:
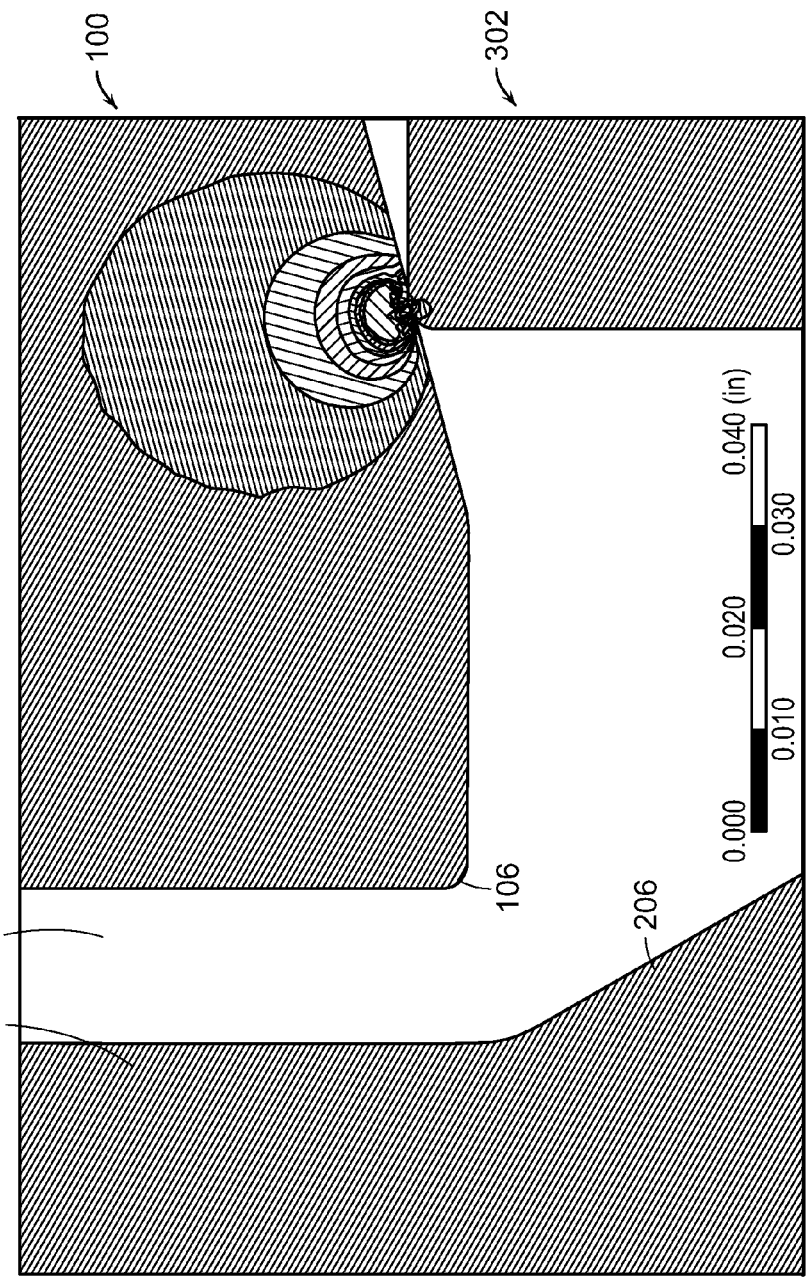

When the needle 200 is pulled through the seat 100, a durable and/or tight seal is created between the angular sealing surface 206 and at least one of the bore edge 106 and the chamfered outlet 104. With reference to FIG. 9B, upon initial contact of the angular sealing surface 206 and the bore edge 106, a plastic deformation of the bore edge 106 may occur. In particular, the plastic deformation can conform the bore edge 106 geometry to a complimentary angular sealing surface 206 geometry. For example, if the bore edge 106 is defined by a pointed junction between the outer side surface 110 and the chamfered outlet 104, the bore edge 106 can plastically deform to a, e.g., sloping, convex, concave, or the like, surface complimentary to the angular sealing surface 206. The plastic deformation occurs, in general, during the first mating between the angular sealing surface 206 and the seat 100. However, it should be understood that the plastic deformation may occur after the first mating between the angular sealing surface 206 and the seat 100. The material of fabrication, e.g., the modulus of elasticity of the material of fabrication, for the seat 100 can be selected such that a plastic deformation only occurs at the bore edge 106 and does not continue to plastically deform during the lifetime of the seat 100. Upon the initial plastic deformation, the bore edge 106 surface complimentary to the angular sealing surface 206 ensures an enhanced seal between said elements. Thus, rather than a seal at a pointed junction between the bore edge 106 and the angular sealing surface 206, the larger contact and/or sealing surface area, i.e., the plastically deformed bore edge 106, reduces the chance of leakage through the seal. With reference to FIG. 9C, in other embodiments, the seat 100 can further yield and/or plastically deform when securely clamped in the seat retainer 302.

Still with reference to FIG. 9A, the exemplary needle 200 can include a groove 208 for a retaining mechanism, such as a snap ring, at a distal end of the needle stem 204. The groove 208 can be configured and dimensioned to mate with, e.g., a collar, bushing, washer, or the like, to securely attach the distal end of the needle stem 204 to a stem return spring mechanism. The needle face 214 of the needle head 202 can include a plurality of head grooves 210. Although illustrated with two perpendicularly positioned head grooves 210 in FIG. 9A, in other embodiments, the needle head 202 can include more and/or less head grooves 210, e.g., zero, one, two, three, four, five, and the like, positioned as, e.g., parallel, differently angled, or the like, head grooves 210. For example, the needle head 202 may not include head grooves 210 and would therefore be defined by a substantially flat needle face 214. As a further example, the needle head 202 may include four head grooves 210 positioned at about 45° relative to each other. The head grooves 210 can be configured and dimensioned to allow passage of the solvent 24 (e.g., mobile phase media 23) during venting through said grooves, over the needle head 202 and the angular sealing surface 206, through the bore 102 and out of the outlet port 68. In particular, the head grooves 210 can enhance the flow of the solvent 24 (e.g., mobile phase media 23) through the seat 100 by, e.g., reducing the flow resistance created by the needle head 202. Similarly, the needle stem 204 can include stem grooves 212 to enhance the flow of the mobile phase media 23 through the bore 102. Although illustrated with four stem grooves 212 positioned at 90° angles relative to each other around the circumference of the needle stem 204, other embodiments can include more and/or less stem grooves, e.g., zero, one, two, three, four, five, six, and the like. In addition, the stem grooves 212 can extend, e.g., the entire length of the needle stem 204, a partial length of the needle stem 204, or the like.

Figure 10A:
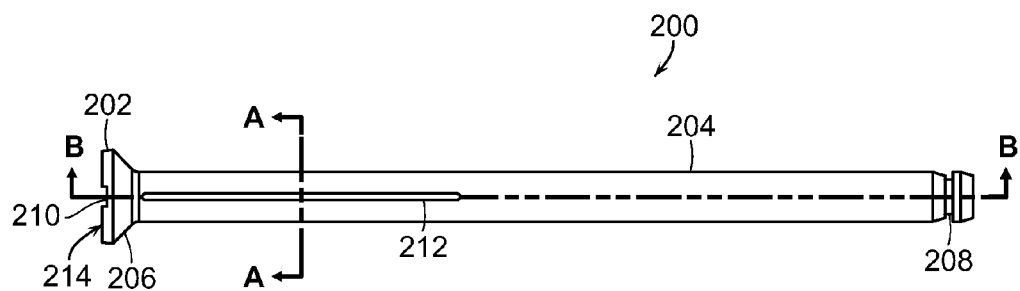
FIG. 10A-D are side, cross-sectional and detailed views of an exemplary embodiment of a needle with stem grooves according to the present disclosure.
Figure 10B:
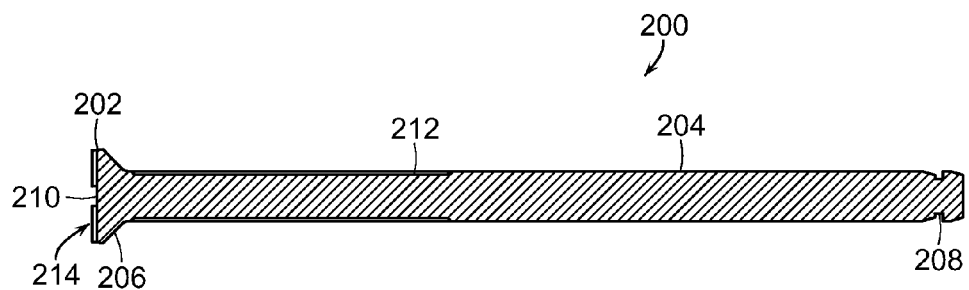

With respect to FIGS. 10A-D, cross-sectional, side and detailed views are provided of the exemplary needle 200. FIG. 10A illustrates a side view of the needle stem 200, including the angular sealing surface 206. In addition, FIG. 10A provides planes "A" and "B" for reference of the cross-sectional views of FIGS. 10B and 10C. The cross-sectional side view of the needle 200 is provided in FIG. 10B along plane "B". As can be seen, the stem grooves 212 create a channel in the needle stem 204. The dimensions of the stem grooves 212, e.g., the depth, width, length, or the like, can be altered as desired to provide larger and/or smaller volumetric area for the flow of the solvent 24 (e.g., mobile phase media 23). It should be understood that a larger volumetric area of the stem grooves 212 results in a larger exposed volume of the vent valve which is required to be filled to reach a desired venting pressure level or to seal off the majority of the vent valve. Thus, a preferred exemplary needle 200 may have small and/or no stem grooves 212.

Figure 10C:
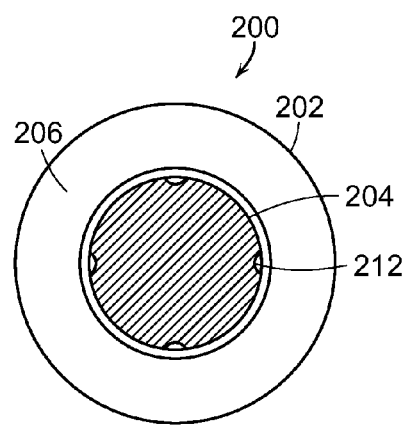
Figure 10D:
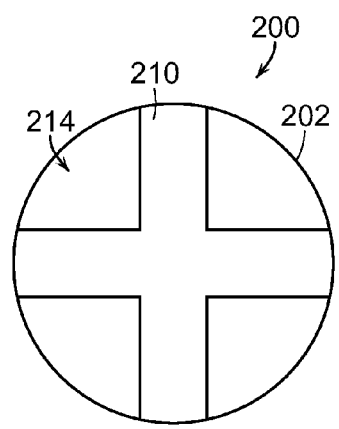

FIG. 10C is a cross-sectional view of the needle 100 along plane "A". In particular, the relationship between the needle head 202 diameter and the needle stem 204 diameter can be seen, i.e., the needle head 202 diameter is greater than the needle stem 204 diameter. In addition, the stem grooves 212 can be seen in the needle stem 204. With reference to FIG. 10D, a front view of the needle face 214 is provided. The needle face 214 can include head grooves 210, e.g., channels, passing across the entire needle face 214 to create a flow path for the mobile phase media 23 when the vent valve 54 is actuated into an open position. It should be understood that once the vent valve 54 is actuated into a closed position, i.e., the angular sealing surface 206 has been pulled against the seat 100, the mobile phase media 23 cannot pass through the contact and/or sealing area of the angular sealing surface 206 and the seat edge 106.

Figure 11:
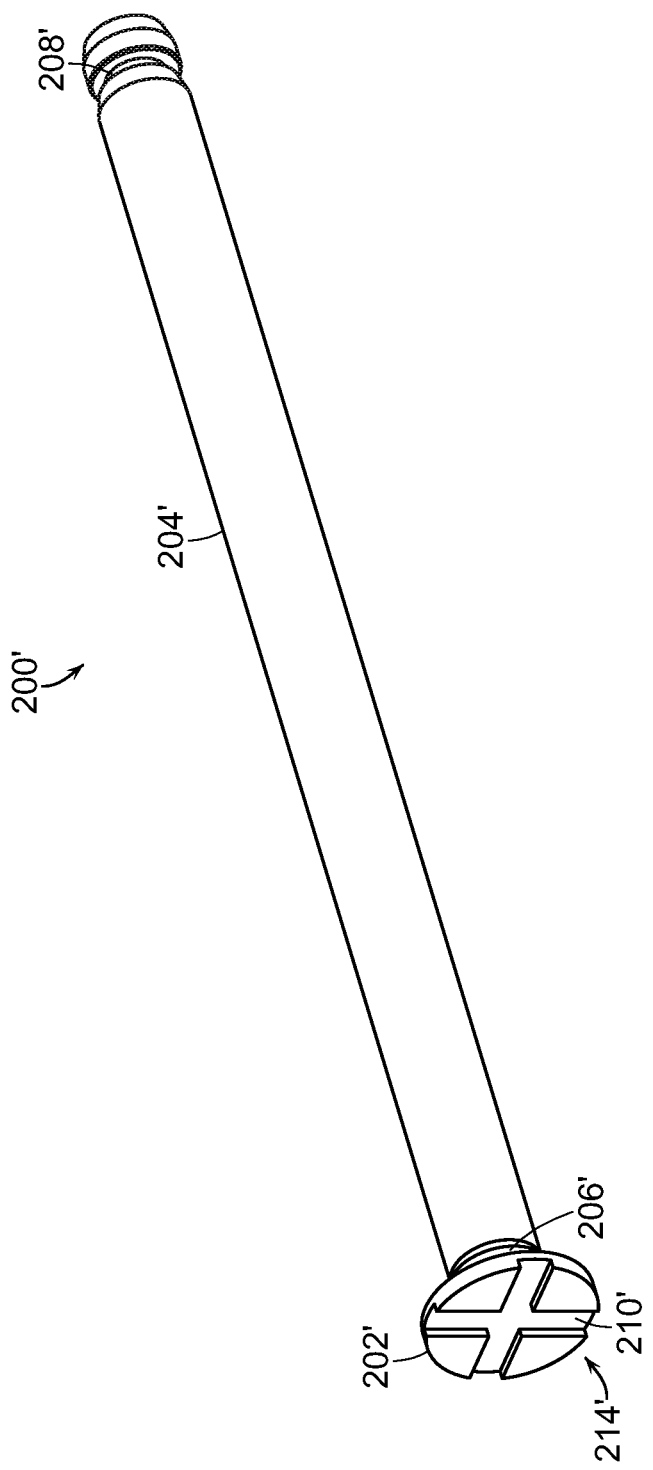
FIG. 11 is an exemplary embodiment of a needle without stem grooves according to the present disclosure.

Turning to FIG. 11, another exemplary embodiment of a needle 200' is illustrated. The needle 200' is substantially similar to the needle 200 previously discussed, including a needle head 202', a needle stem 204' and a groove 208' at a distal end of the needle stem 204'. Additionally, the needle 200' includes an angular sealing surface 206', i.e., a transition region, between the needle head 202' and the needle stem 204'. The needle face 214' of the needle head 202' can further include head grooves 210'. However, similarly to the needle face 214, it should be understood that in other embodiments, the needle face 214' can include more and/or less head grooves 210', e.g., zero, one, two, three, four, and the like. Rather than including stem grooves 212, the exemplary needle stem 204' can be defined by a uniformly dimensioned needle stem 204' surface.

Figure 12A:
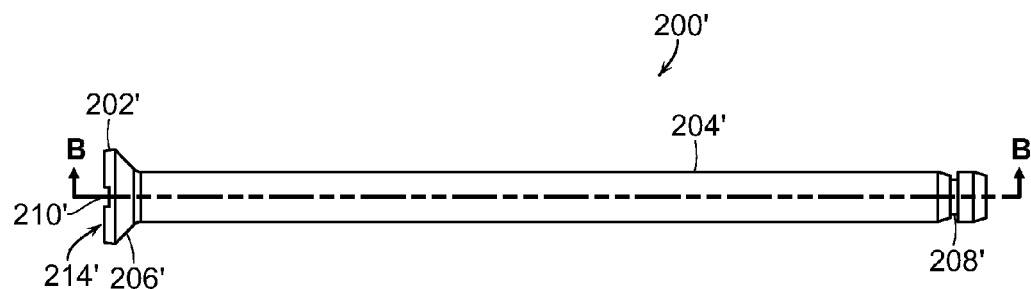
FIGS. 12A and 12B are side and cross-sectional views of an exemplary embodiment of a needle without stem grooves according to the present disclosure.
Figure 12B:
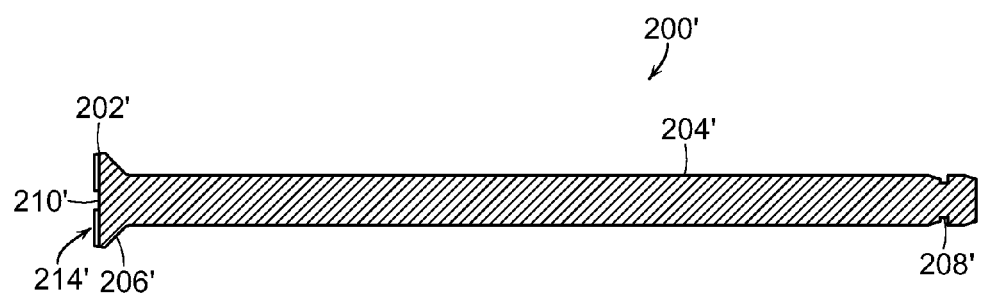

FIGS. 12A and 12B are side and cross-sectional views of the exemplary needle 200'. In particular, FIG. 12A depicts a side view of the needle 200' with a uniformly dimensioned needle stem 204', i.e., a needle stem 204' without stem grooves 212. Plane "B" is depicted as a reference for the cross-sectional view of FIG. 12B. As can be seen in the cross-sectional side view, the needle stem 204' is uniformly dimensioned along the entire length of the needle stem 204' between the groove 208' and the angular sealing surface 206'. A rounded joint, e.g., a fillet, can further connect the angular sealing surface 206' and the needle stem 204'.

Figure 13:
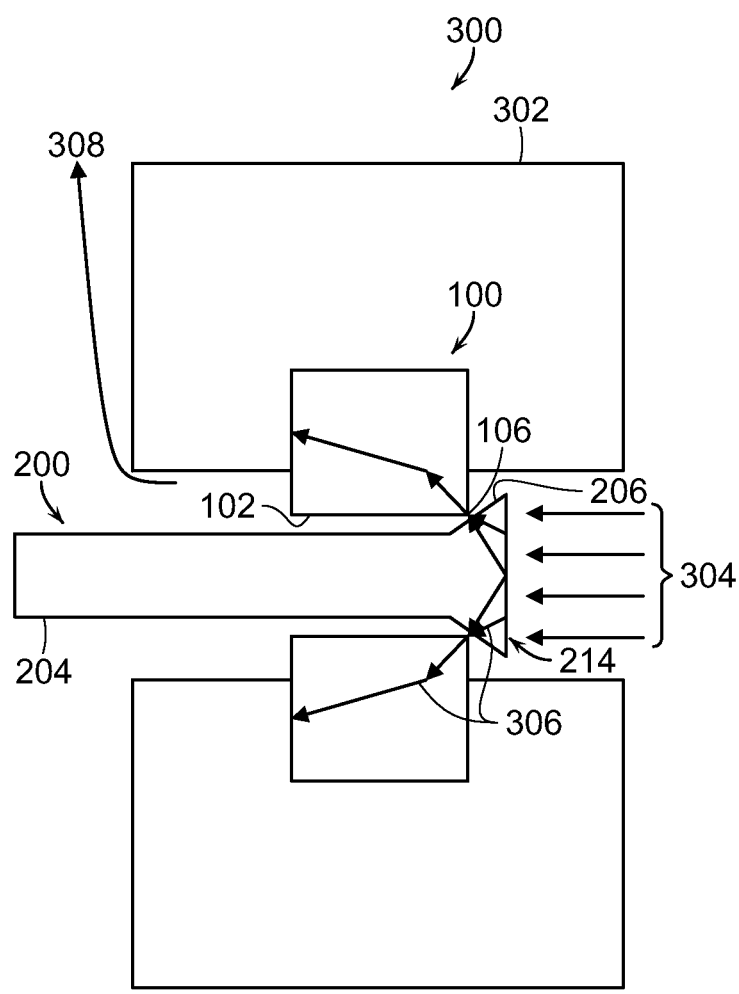
FIG. 13 is an exemplary embodiment of a seat retainer assembly illustrating a pressure assist according to the present disclosure.

Turning now to FIG. 13, a seat retainer assembly 300 is depicted, including a seat retainer 302, a seat 100 and a needle 200. Although referring to a needle 200, it should be understood that the exemplary seat retainer assembly 300 can instead include a needle 200'. The seat retainer 302 can be securely disposed inside the vent valve head section 70 of FIG. 6. The seat 100 can be securely disposed inside the seat retainer 302. As described above, although not illustrated in FIG. 13, the seat 100 can be secured within the seat retainer 302 with protrusions, e.g., ridges, spikes, or the like, located on the internal contact surface of the seat retainer 302, which can act to prevent undesired movement of the seat 100 in the seat retainer 302. The needle stem 204 is at least partially disposed inside the bore 102 of the seat 100 and can be translated within the bore 102. The groove 208 at the distal end of the needle stem 204 can be secured to a stem return spring mechanism (not shown).

Flow of the mobile phase media 23 can enter the seat retainer assembly 300 through the inlet port 66 and can proceed in the direction illustrated by inlet arrows 304. Although illustrated in a closed position, i.e., the angular sealing surface 206 is pressed against the bore edge 106, it should be understood that in an open position, an open flow path between the bore edge 106 and the angular sealing surface 206 is available for the mobile phase media 23 to pass through unimpeded. The open flow path, i.e., annular gap, can be in the range of, e.g., about 0.005 to 0.010 inches. Thus, the solvent 24 (e.g., mobile phase media 23) can enter through the inlet port 66, flow over the needle face 214 and the angular sealing surface 206 into the bore 102, and can further vent and/or flow out of the outlet port 68 in the direction shown by the outlet arrow 308. As would be understood by those of skill in the art, rather than an open and/or unfilled bore 102 which creates a large exposed volume, the exemplary seat retainer assembly 300 includes a bore 102 with a needle stem 204 passing therethrough to reduce the exposed volume. The reduced exposed and/or internal volume within the bore 102 enhances the ability of a user to control the pressure in the vent valve 54 and, thus, the system 10. For example, in a closed position, the needle stem 204 passing through the bore 102 seals off the majority of the exemplary vent valve, thereby leaving only the volume of the inlet port 66 and the small actuation area between the inlet port 66 and the needle face 214 exposed to the system 10.

The exemplary pull-through needle 200 configuration of FIG. 13 further permits the use of a pressure assist from the system pressure to seal the angular sealing surface 206 against the seat edge 106 and/or the seat 100. In particular, to actuate the vent valve 54 into a closed position, the stem 204 can be pulled through the bore 102 in a downstream direction to press the angular sealing surface 206 against the bore edge 106 and/or the seat 100. As would be understood by those of skill in the art, the flow of the mobile phase media 23 from the inlet port 66 enters the seat retainer assembly 300 as indicated by the inlet arrows 304. Thus, the mobile phase media 23 creates a pressure force due to the pressure of the system 10 on the needle face 214. In particular, the added force created by the mobile phase media 23 can be represented by Equation 1 below.

$$F = P \times SA \qquad (1)$$

wherein F is the added closing force created by the mobile phase media 23, P is the system pressure on the needle face 214, and SA is the needle 200/stem 100 sealed area, which can be further represented by Equation 2.

$$SA = \pi \times r^2 \qquad (2)$$

wherein r is the seal radius, i.e., the radius of the contact seal between the angular sealing surface 206 and the bore edge 106. An adjustment of the seal radius and/or diameter can therefore vary the amount of pressure assist created by the system 10.

The pressure force on the needle face 214 assists in translating the needle stem 204 through the bore 102 and further assists in pressing and/or sealing the angular sealing surface 206 against the bore edge 106. The added pressure force on the needle face 214 is thereby supported through the sealing surface, i.e., the contact area between the bore edge 106 and the angular sealing surface 206, to enhance the seal and/or improve the sealing stress between said components.

As illustrated by the load path arrows 306, the pressure assist force creates a pressure load which passes through the needle head 202, the needle face 214 and/or the angular sealing surface 206 and is further transmitted into the seat 100. In turn, the seat 100 transmits the pressure load into the seat retainer 302, which absorbs the pressure forces, thereby providing support for the seat 100 and the needle 200 and/or prevents transmission of the pressure forces to other components of the assembly.

It should be understood that, e.g., the diameter of the sealing surface, the diameter of the bore 102, the diameter of the bore edge 106, the chamfered edge 104, the diameter of the needle stem 204, the diameter of the needle face 214, and the like, can be configured and dimensioned to modify the pressure assist created by the system pressure, as was previously discussed with respect to Equations 1 and 2. For example, the diameter of the needle face 214 can be increased to create a larger surface area upon which the pressure forces act, thereby increasing the pressure assist and/or sealing the angular sealing surface 206 against the bore edge 106. In contrast, the diameter of the needle face 214 can be decreased to reduce the surface area upon which the pressure forces act, thereby decreasing the pressure assist and/or sealing the angular sealing surface 206 against the bore edge 106. The materials of fabrication of the needle 200 and the seat 100 can further be selected to prevent damage of said components when a pressure assist force is introduced against the needle face 214.

Figure 14:
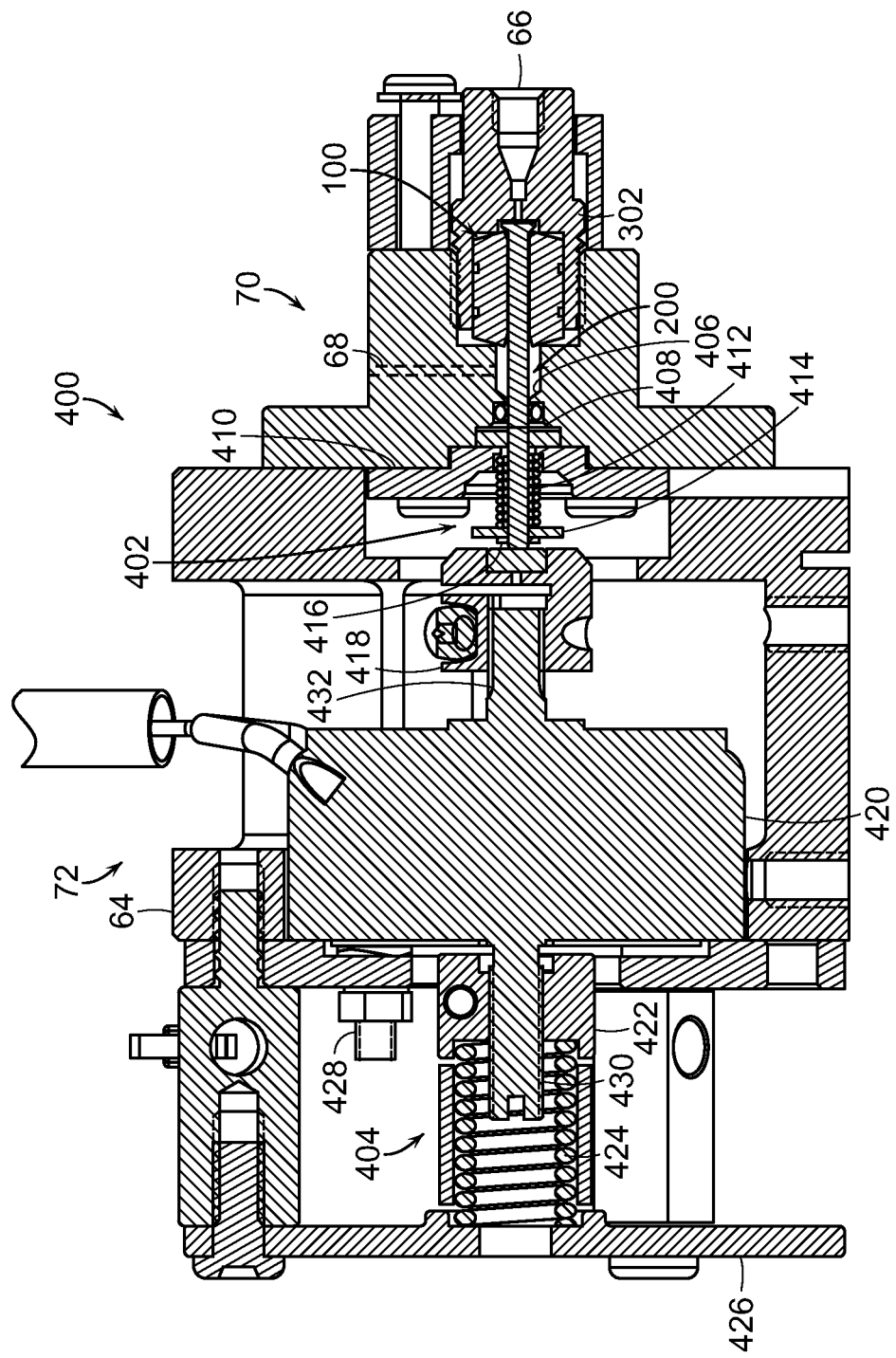
FIG. 14 is an exemplary embodiment of a vent valve in an open position according to the present disclosure.

Turning now to FIG. 14, an exemplary embodiment of a vent valve 400, e.g., a solenoid valve, is depicted in an open position, i.e., a flow path exists between the angular sealing surface 206 of the needle 200 and the bore edge 106 of the seat 100. The vent valve 400 includes a valve body 64, which includes a vent valve actuator section 72 and a vent valve head section 70. The seat retainer assembly 300 is securely disposed inside the vent valve head section 70, including the seat retainer 302, the seat 100 and the needle 200. The vent valve head section 70 further includes the inlet port 66 and the outlet port 68.

A stem return spring mechanism 402 disposed inside the valve body 64 can include, e.g., a stem return spring 412, a collar 414 and a retaining ring 416. Other types of retaining mechanisms can be used in place of the retaining ring 46. For example, a spring pin can be used in place of the retaining ring 46. The stem return spring mechanism 402 can be securely connected to a distal end of the needle stem 204 with respect to the needle head 202. The collar 414 and the retaining ring 416 can have an inner bore dimensioned to fit around the needle stem 204. In particular, the collar 414 can be securely fastened to the retaining ring 416, which in turn can be securely mounted around the needle stem 204 in the groove 208. The retaining ring 416 may be configured and dimensioned to "snap" fit into the groove 208. The retaining ring 416 can be, e.g., an e-ring, which snaps into the groove 208. Alternatively, a spring pin and a hole in the needle stem 204 can be implemented. In other embodiments, alternative low profile axial retaining mechanisms known in the art may be used. The stem return spring 412 can be disposed around the needle stem 204 and can provide pressure directly against the collar 414 and a stem return spring plate 410. The stem return spring plate 410 can be securely fastened to the valve body 64. The needle stem 204 can further translate through a bore in the stem return spring plate 410.

The stem return spring 412 can be compressed by applying a compression force on the distal end of the needle stem 204 and, thereby, the collar 414, in the direction of the stem return spring plate 410. The motion of compressing the stem return spring 412 actuates the vent valve 400 into an open position. In particular, as the stem return spring 412 is compressed, the needle stem 204 translates through the bore 102 and creates a flow path opening between the angular sealing area 206 and the bore edge 106. As should be understood by those of skill in the art, when the stem return spring 412 is in a compressed state between the stem return spring plate 410 and the collar 414, the mechanical energy stored in the stem return spring 412 provides an expansion force against said components to expand the stem return spring 412 to its natural length. When the stem return spring 412 expands, the force against the collar 414 and the stem return spring plate 410 translates the needle stem 204 through the bore 102 in a direction away from the stem return spring plate 410. The vent valve 400 is thereby actuated into a closed position, i.e., the stem return spring 412 pulls the needle stem 204 through the bore 102 sufficiently to provide a sealing stress between the angular sealing surface 206 and the bore edge 106. The pressure assist previously discussed can enhance the sealing stress, i.e., the sealing force, on the seal.

On a side opposing the stem return spring 412, the stem return spring plate 410 can include a stem seal 408, e.g., an ACQUITY BSM seal, securely disposed around the needle stem 204 and between the stem return spring plate 410 and the valve body 64 (see, e.g., Waters Technologies Corporation, Massachusetts, USA, Head Plunger Seal, Product Number 700002599 (2011)). The stem seal 408 can ensure a waterproof and/or pressure resistant seal between the vent valve head section 70 and the return spring mechanism 402 and/or the vent valve actuator section 72, e.g., to prevent leakage of the mobile phase media 23 through the bore in which the needle stem 204 is situated. Further, the vent valve head section 70 includes a cavity 406 into which the mobile phase media 23 flows after passing through the bore 102. The stem seal 408 ensures that the solvent 24 (e.g., mobile phase media 23) flowing into the cavity 406 creates a pressure sufficient to vent the mobile phase media 23 out of the vent valve 400 through the outlet port 68.

Still with reference to FIG. 14, the vent valve actuator section 72 includes the solenoid return spring mechanism 404 which further includes a solenoid return spring 424, a solenoid stroke calibration collar 422, a stem/solenoid calibration collar 418 and an actuator 420. In particular, the solenoid stroke calibration collar 422 can be securely fastened to a rear shaft 430 of the actuator 420. The solenoid stroke calibration collar 422 and the rear shaft 430 of the solenoid can be, e.g., threaded, or the like, to permit a calibration and/or adjustment of the position of the solenoid stroke calibration collar 422 along the rear shaft 430. The solenoid stroke calibration collar 422 can further include a clamping feature for enhanced adjustment along and/or attachment to the rear shaft 430. Thus, the compression and/or expansion forces produced by the solenoid return spring 424 can be adjusted for a desired system pressure being implemented. The solenoid return spring 424 can be disposed around the rear shaft 430 and between the solenoid stroke calibration collar 422 and a solenoid return spring plate 426. Further, the solenoid return spring 424 can be securely attached to the solenoid stroke calibration collar 422 and/or the solenoid return spring plate 426. The solenoid return spring plate 426 can be securely mounted to the valve body 64. Thus, the solenoid return spring 424 can be compressed and/or expanded between the solenoid return spring plate 426 and the solenoid stroke calibration collar 422. As would be understood by those of skill in the art, a compression and/or expansion of the solenoid return spring 424 transmits the compression and/or expansion force to the solenoid stroke calibration collar 422, which in turn translates the actuator 420 towards and/or away from the solenoid return spring plate 426. An actuator guide protrusion 428 can pass through a bore of the valve body 64 and can assist in guiding the actuator 420 along an even and/or straight path. Although illustrated with one actuator guide protrusion 428, it should be understood that a greater and/or lesser number of actuator guide protrusions 428 can be implemented, e.g., zero, one, two, three, four, or the like.

A collar protrusion 432 extending from an actuator 420 side opposing the solenoid return spring 424 can be utilized for attachment of the stem/solenoid calibration collar 418. The collar protrusion 432 and the stem/solenoid calibration collar 418 can be, e.g., threaded, or the like, to permit a calibration and/or adjustment of the position of the stem/solenoid calibration collar 418 along the collar protrusion 432. The stem/solenoid calibration collar 418 can further include a clamping feature for enhanced adjustment along and/or attachment to the collar protrusion 432. Thus, the distance of translation of the stem/solenoid calibration collar 418 can be adjusted for a desired system pressure being implemented. The stem/solenoid calibration collar 418 can be in communication with the stem return spring mechanism 402. In particular, the stem/solenoid calibration collar 418 can, e.g., provide and/or remove a force against the distal end of the needle stem 204 to translate the needle stem 204 through the bore 102 to actuate the vent valve 400 into one of an open position and a closed position, respectively.

Figure 15:
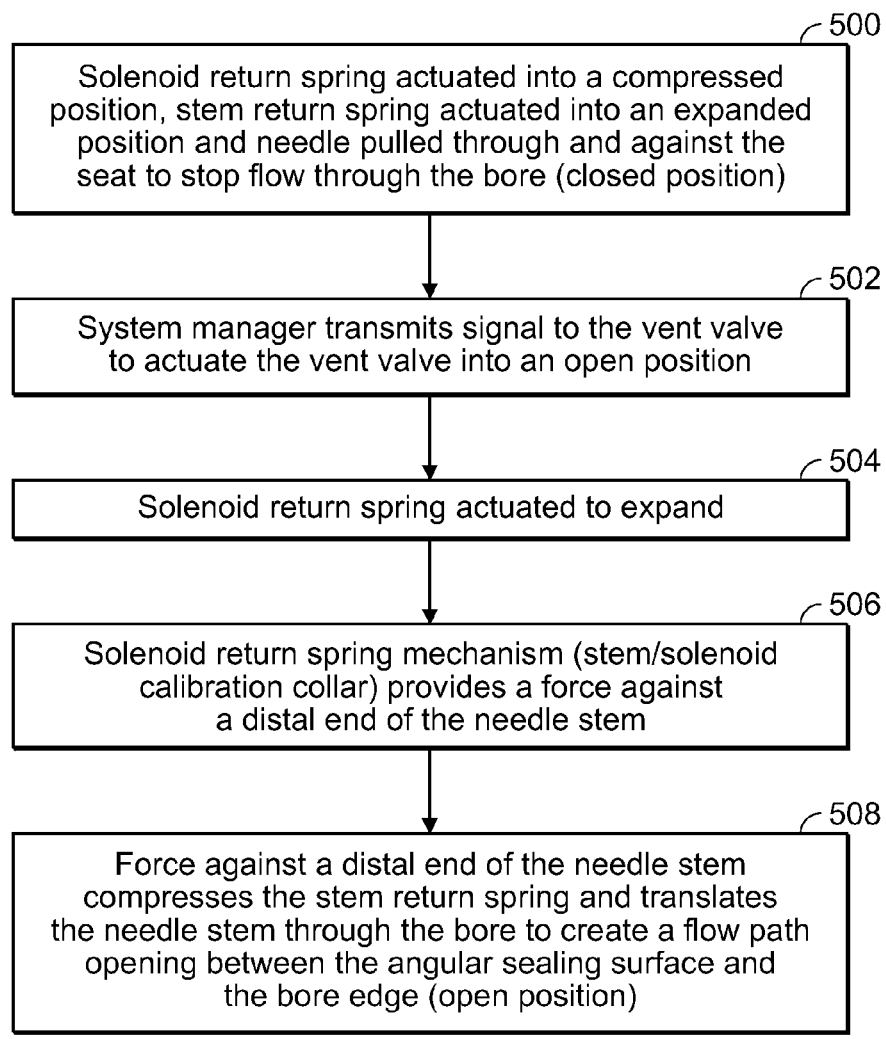
FIG. 15 is a block diagram for actuating an exemplary embodiment of a pull-through normally closed vent valve into an open position according to the present disclosure.

The exemplary vent valve 400 can be configured as one of a pull-through normally closed valve or a pull-through normally open valve. With respect to the pull-through normally closed valve and the block diagram of FIG. 15, the spring constants for the stem return spring 412 and the solenoid return spring 424 can be adjusted according to the operational pressure to ensure that the stem return spring 412 is normally expanded and the solenoid return spring 424 is normally actuated into a compressed position (500). Alternatively, the solenoid can be flipped to disengage from the head section 70 when the solenoid valve 400 has been actuated into a closed position. As discussed previously, the expanded setting of the stem return spring 412 provides an expansion force against the stem return spring plate 410, which in turn pulls the needle stem 204 through the bore to actuate the vent valve 400 into a closed position, i.e., the angular sealing surface 206 of the needle head 202 is pulled tightly against the bore edge 106 of the seat 100 to stop flow through the bore 102 (500). The compressed setting of the solenoid return spring 424 translates and/or retracts the actuator 420 and the stem/solenoid calibration collar 418 in a direction away from the stem return spring mechanism 402. Thus, the stem/solenoid calibration collar 418 does not provide a force against the distal end of the needle stem 204 when the solenoid return spring 424 is compressed. The system/convergence manager 20, discussed previously, is in communication with the vent valve 400 and can transmit a signal to the vent valve 400 to expand the solenoid return spring 424 to actuate the vent valve 400 into an open position (502). As would be understood by those of skill in the art, when the solenoid return spring 424 is actuated to expand (504), the expansion force generates a force by the stem/solenoid calibration collar 418 against the distal end of the needle stem 204 (506). The spring constant of the solenoid return spring 424 can be selected such that the force generated against the distal end of the needle stem 204 is sufficient to overcome the expansion force of the stem return spring 412. Thus, as the solenoid return spring 424 expands, the stem return spring 412 is compressed and the needle stem 204 is translated through the seat 100 to create an opening between the angular sealing surface 206 and the bore edge 106, i.e., the vent valve 400 is actuated into an open position (508).

Figure 16:
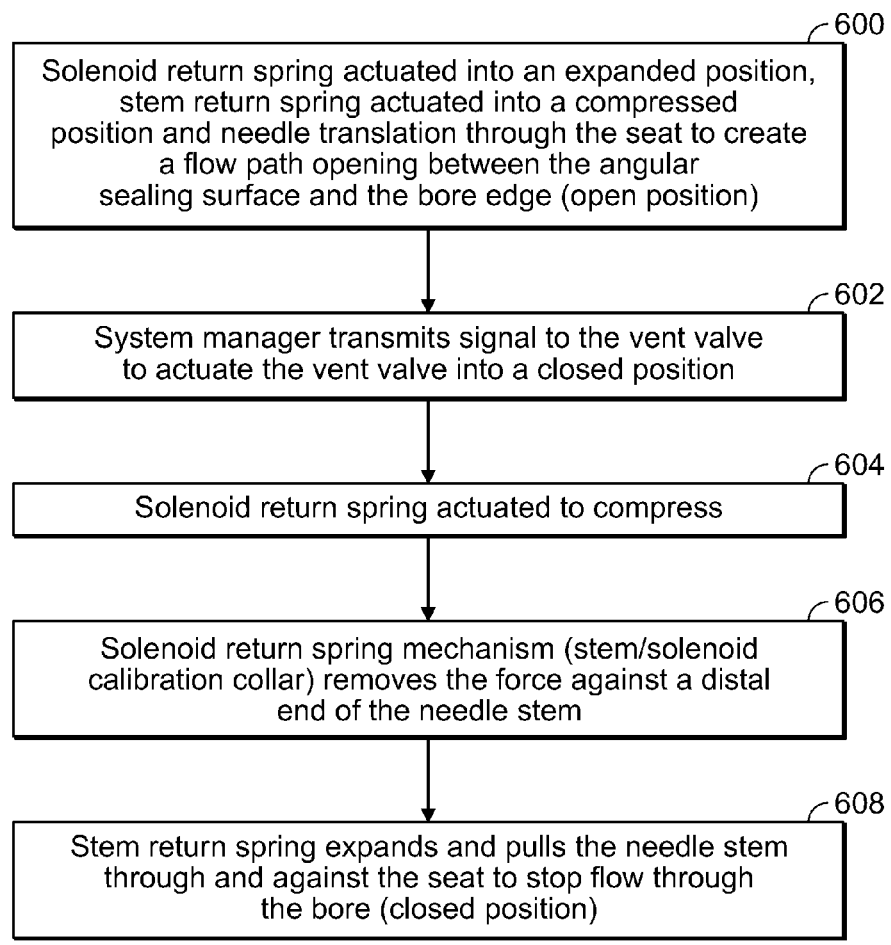
FIG. 16 is a block diagram for actuating an exemplary embodiment of a pull-through normally open vent valve into a closed position according to the present disclosure.

With respect to the pull-through normally open valve and the block diagram of FIG. 16, the spring constants for the stem return spring 412 and the solenoid return spring 424 can be adjusted according to the operational pressure to ensure that the stem return spring 412 is normally compressed and the solenoid return spring 424 is normally actuated into an expanded position (600). As discussed previously, the expanded setting of the solenoid return spring 424 translates the actuator 420 and the stem/solenoid calibration collar 418 in the direction of the stem return spring mechanism 402. Thus, the stem/solenoid calibration collar 418 provides a force against the distal end of the needle stem 204 when the solenoid return spring 424 is expanded, causing the stem return spring 412 to compress. In particular, the spring constant of the solenoid return spring 424 can be selected such that it overcomes the spring constant of the stem return spring 412. The compressed setting of the stem return spring 412, in conjunction with the force on the distal end of the needle stem 204, provides a pulling force on the collar 414, which in turn translates the needle stem 204 through the bore to actuate the vent valve 54 into an open position, i.e., a flow opening exists between the angular sealing surface 206 of the needle head 202 and the bore edge 106 of the seat 100 to permit flow through the bore 102 (600). The system/convergence manager 20, discussed previously, is in communication with the vent valve 54 and can transmit a signal to the vent valve 54 to compress the solenoid return spring 424 to actuate the vent valve 54 into a closed position (602). As would be understood by those of skill in the art, when the solenoid return spring 424 is actuated to compress (604), the force on the distal end of the needle stem 204 by the stem/solenoid calibration collar 418 is removed (606). The spring constant of the stem return spring 412 can be selected such that when the force generated against the distal end of the needle stem 204 is removed, the stem return spring 412 can automatically expand to close the vent valve 54. Thus, as the solenoid return spring 424 compresses, the stem return spring 412 expands and translates the collar 414 in a direction away from the stem return spring plate 410, thereby pulling the needle stem 204 through the seat 100 to create a durable and/or tight seal between the angular sealing surface 206 and the bore edge 106, i.e., the vent valve 54 is actuated into a closed position (608).

Figure 17:
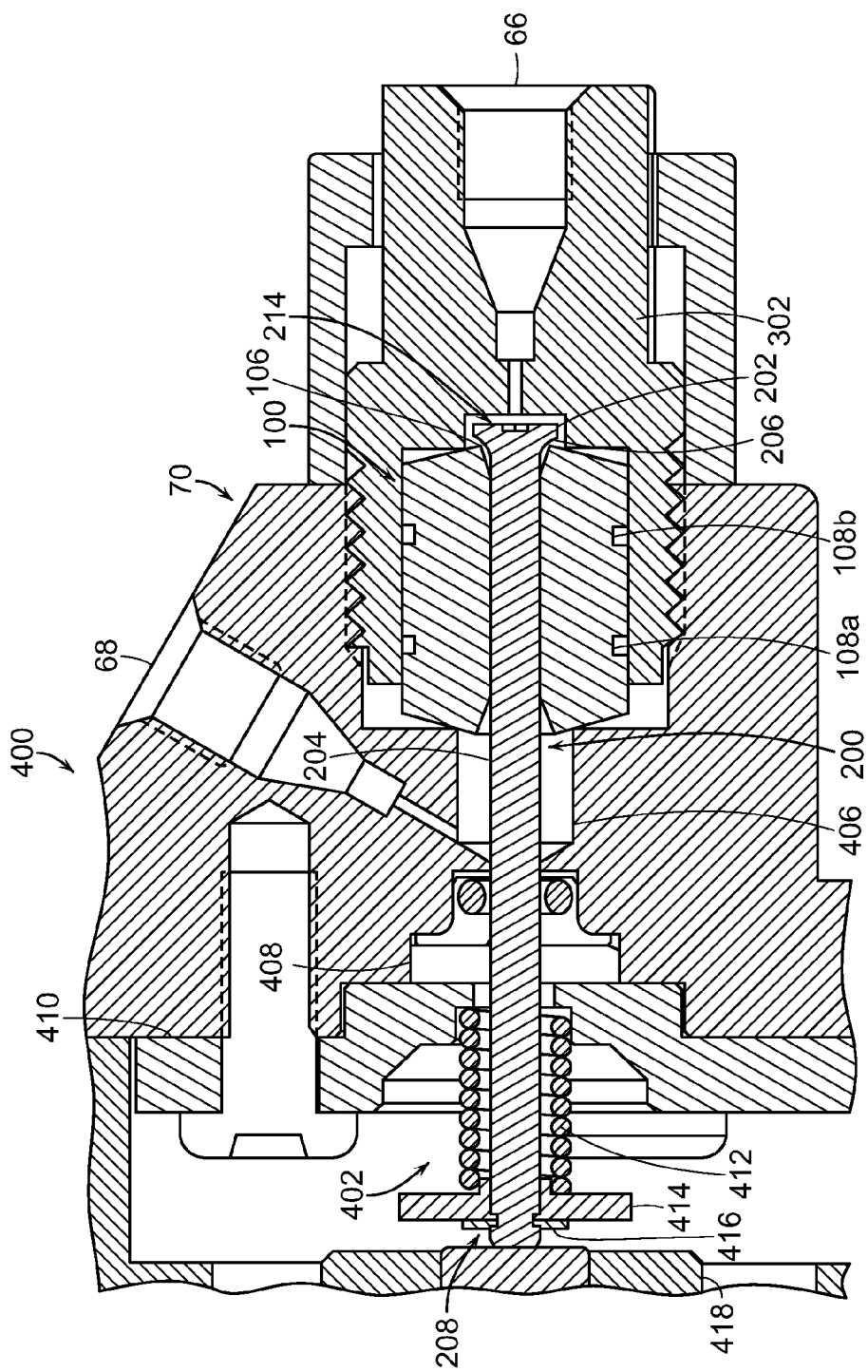
FIG. 17 is a detailed view of an exemplary embodiment of a vent valve in an open position according to the present disclosure.

Turning now to FIG. 17, a detailed cross-sectional view of the exemplary vent valve 400 is provided with specific focus on the vent valve head section 70 in an open configuration. The seat is securely disposed inside the seat retainer 302. The seat retainer 302 can be securely fastened inside the vent valve head section 70 by, e.g., matching threading on an outer surface of the seat retainer 302 and an inner surface of the valve body 64. The vent valve 400 is illustrated actuated into an open position, i.e., a flow path exists between the angular sealing surface 206 and the bore edge 106.

Figure 18:
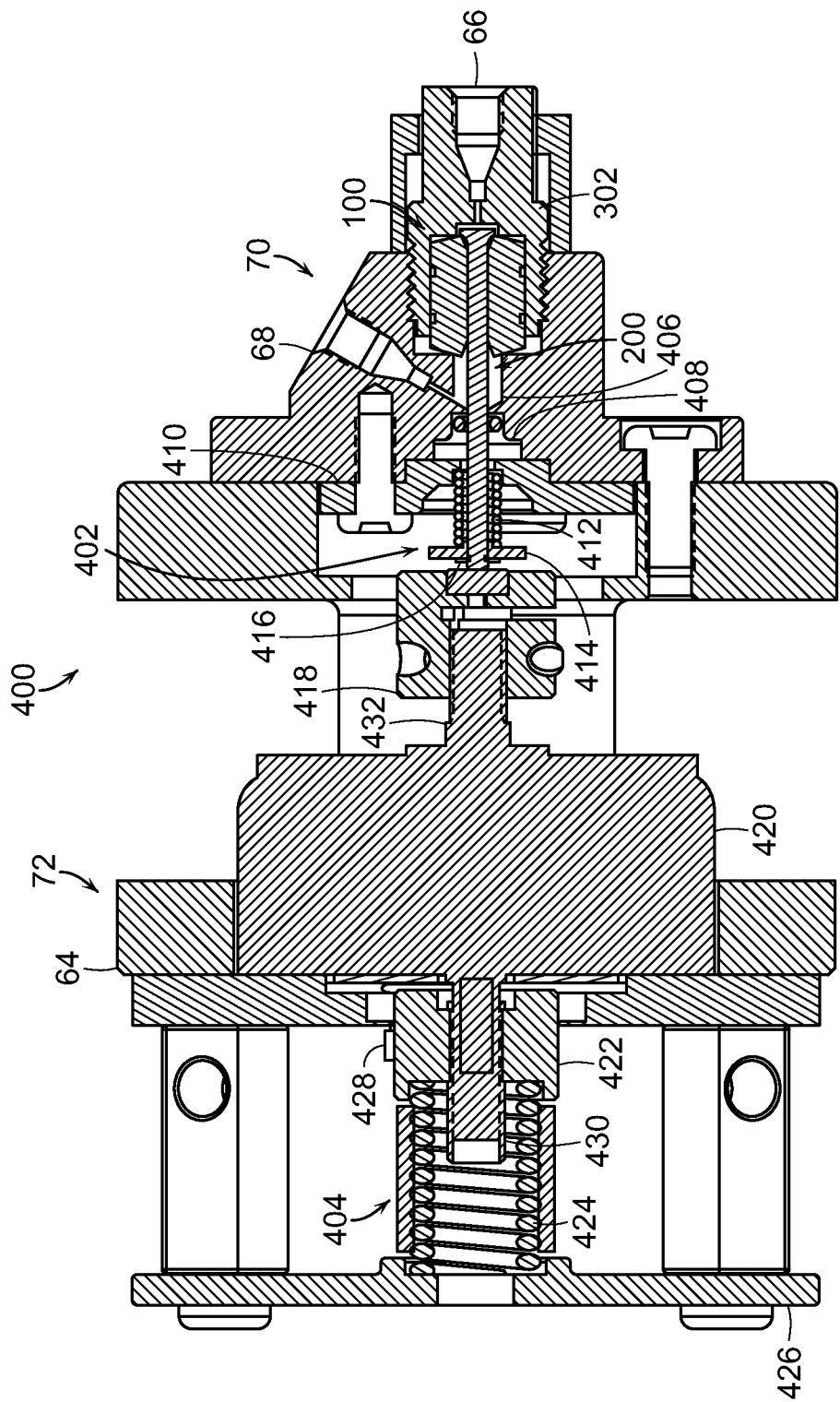
FIG. 18 is an exemplary embodiment of a vent valve in a closed position according to the present disclosure.

With reference now to FIG. 18, an exemplary embodiment of the vent valve 400, e.g., a solenoid valve, is depicted in a closed position, i.e., a durable and/or tight seal is created between the angular sealing surface 206 of the needle 200 and the bore edge 106 of the seat 100. The components of the vent valve 400 of FIG. 16 are substantially similar in configuration and/or function as those described with respect to the vent valve 400 of FIGS. 14 and 15. However, the actuation of the vent valve 400 of FIG. 16 into a closed position actuates the solenoid return spring mechanism 404 to permit the stem return spring mechanism 402 to pull the needle 200 through the seat 100 to stop flow through the bore 102. In particular, as the stem return spring mechanism 402 pulls the needle 200 through the seat 100, a durable and/or tight waterproof seal is created between the angular sealing surface 206 of the needle 200 and the bore edge 106 of the seat 100.

Figure 19A:
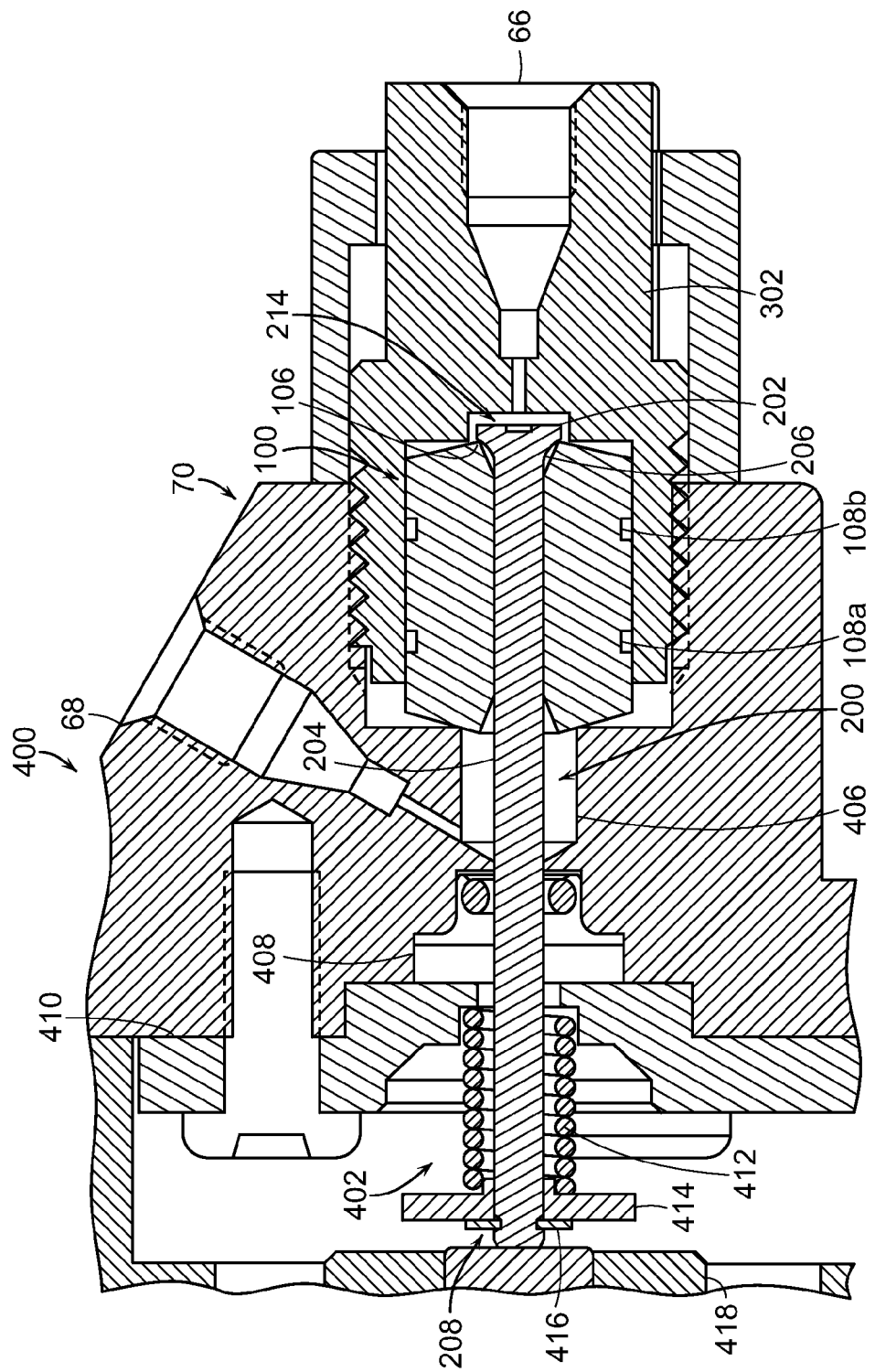
FIGS. 19A and 19B are detailed views of an exemplary embodiment of a vent valve in a closed position according to the present disclosure.
Figure 19B:
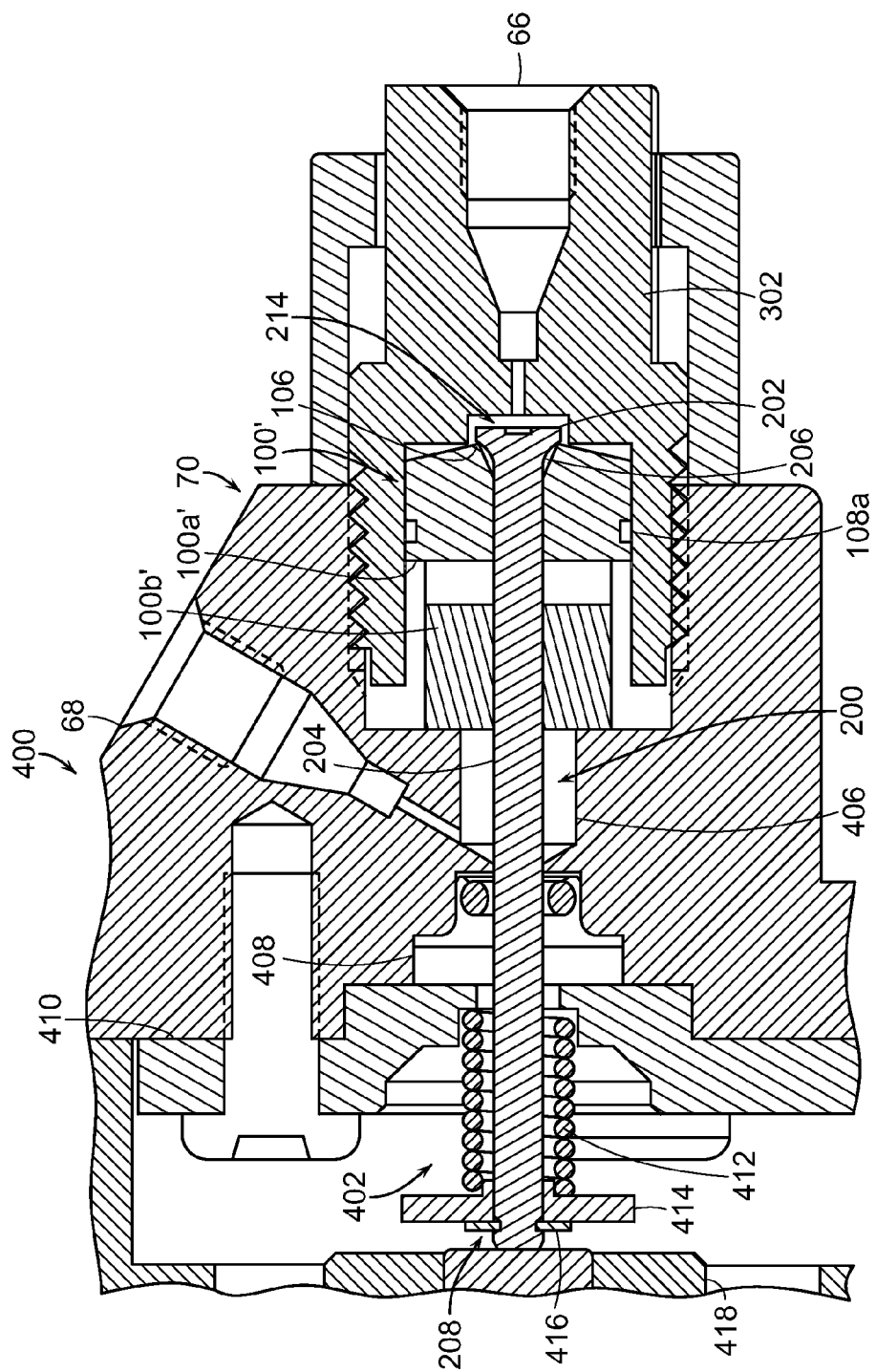

FIG. 19A is a detailed cross-sectional view of the exemplary vent valve 400, with specific focus on the vent valve head section 70 in a closed configuration. As previously discussed, the closed configuration and/or position is created by actuating the solenoid return spring mechanism 404 to permit the stem return spring mechanism 402 to pull the needle 200 through the seat 100 to stop flow through the bore 102. The durable and/or tight waterproof seal between the angular sealing surface 206 and the bore edge 106 prevents leakage of the mobile phase media 23 therebetween. As discussed above, although illustrated as a seat 100 having a unitary structure, it should be understood that in some exemplary embodiments, the seat 100 can include a plurality of components. For example, FIG. 19B shows a cross-sectional view of an exemplary vent valve 400 that includes a dual component seat 100'. In particular, seat 100' includes a seal portion 100a' and a bushing 100b' mechanically coupled relative to each other. The seal portion 100a' functions substantially similarly to the seat 100 described above and acts to create a seal between the seat 100' and the needle 200 when the needle 200 is pulled through the seat 100'. The bushing 100b' provides a surface along which the needle 200 can be smoothly translated.

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the technology.

The invention claimed is:

1. A vent valve, comprising:
a valve body that includes a seat retainer, a needle and a seat, the needle including a needle stem and a needle head, the seat including a bore extending between two outer side surfaces of the seat, the bore including a substantially uniformly extending inner bore defined by an inner bore diameter and outwardly sloping, angled outlets extending continuously from both sides of the inner bore diameter of the substantially uniformly extending inner bore to a bore edge at the respective outer side surface of the seat, the outer side surfaces of the seat being angled towards each other;
wherein the seat is disposed inside the seat retainer;
wherein the needle stem is disposed inside the bore; and
wherein the needle is configured to be pulled through the seat to position the needle head against the bore edge to stop flow through the bore.

2. The vent valve of claim 1, wherein the needle is configured to be pushed through the seat to start flow through the bore.

3. The vent valve of claim 1, wherein the needle comprises an exterior coating.

4. The vent valve of claim 3, wherein the exterior coating is at least one of a gold coating, a platinum coating, a ceramic coating, and a polymer coating.

5. The vent valve of claim 1, wherein a needle head diameter is greater than a needle stem diameter.

6. The vent valve of claim 5, wherein the needle comprises an angular sealing surface between the needle stem and the needle head for self-centering and aligning the needle during translation through the seat.

7. The vent valve of claim 6, wherein the angular sealing surface is pulled against the bore edge of the seat to stop flow through the bore.

8. The vent valve of claim 7, wherein a plastic deformation of the bore edge occurs during pulling of the angular sealing surface against the bore edge.

9. The vent valve of claim 8, wherein the plastic deformation conforms the bore edge geometry to a complimentary angular sealing surface geometry.

10. The vent valve of claim 9, wherein the plastic deformation of the bore edge geometry ensures a tight seal against the angular sealing surface.

11. The vent valve of claim 5, wherein an inner bore diameter is greater than the needle stem diameter.

12. The vent valve of claim 1, where the needle head comprises at least one head groove on a needle head face extending in a direction perpendicular to a longitudinal axis defined by the needle stem.

13. The vent valve of claim 1, wherein the needle stem comprises at least one stem groove extending in a direction parallel to a longitudinal axis defined by the needle stem.

14. The vent valve of claim 1, wherein pulling the needle through the seat to stop flow through the bore reduces an exposed volume of the valve body.

15. The vent valve of claim 1, wherein the seat is fabricated from at least one of a 30% carbon fiber filled PEEK material, a filled or unfilled grade PEEK, and a filled or unfilled grade of polyimide plastic.

16. The vent valve of claim 10, comprising a pressure force to enhance the tight seal against the angular sealing surface.

17. The vent valve of claim 1, wherein the seat comprises a unitary structure.

18. The vent valve of claim 1, wherein the seat comprises a plurality of components.

19. A method of closing a vent valve, comprising:
providing a valve body that includes a seat retainer, a needle and a seat, the needle including a needle stem and a needle head, the seat including a bore extending between two outer side surfaces of the seat, the bore including a substantially uniformly extending inner bore defined by an inner bore diameter and outwardly sloping, angled outlets extending continuously from both sides of the inner bore diameter of the substantially uniformly extending inner bore to a bore edge at the respective outer side surface of the seat, the outer side surfaces of the seat being angled towards each other;
wherein the seat is disposed inside the seat retainer;
wherein the needle stem is disposed inside the bore; and
pulling the needle through the seat to position the needle head against the bore edge to stop flow through the bore.

20. The method of claim 19, wherein a needle head diameter is greater than a needle stem diameter.

21. The method of claim 20, wherein the needle comprises an angular sealing surface between the needle stem and the needle head for self-centering and aligning the needle during translation through the seat.

22. The method of claim 21, comprising pulling the angular sealing surface against the bore edge of the seat to stop flow through the bore.

23. The method of claim 22, comprising plastically deforming the bore edge geometry to a complimentary angular sealing surface geometry.

24. The method of claim 23, wherein plastically deforming the bore edge geometry ensures a tight seal against the angular sealing surface.

25. The method of claim 24, comprising providing a pressure force to enhance the tight seal against the angular sealing surface.

26. A system for closing a vent valve, comprising:
a valve body that includes a seat retainer, a needle, a seat, a stem return spring mechanism and a solenoid return spring mechanism, the needle including a needle stem and a needle head, the seat including a bore extending between two outer side surfaces of the seat, the bore including a substantially uniformly extending inner bore defined by an inner bore diameter and outwardly sloping, angled outlets extending continuously from both sides of the inner bore diameter of the substantially uniformly extending inner bore to a bore edge at the respective outer side surface of the seat, the outer side surfaces of the seat being angled towards each other;
wherein the seat is disposed inside the seat retainer;
wherein the needle stem is disposed inside the bore;
wherein the stem return spring mechanism connects to a distal needle stem end opposing the needle head;
wherein the solenoid return spring mechanism is in communication with the stem return spring mechanism; and
a processing device configured to actuate the solenoid return spring mechanism to permit the stem return spring mechanism to pull the needle through the seat to position the needle head against the bore edge to stop flow through the bore.

* * * * *